US009289496B2

(12) United States Patent
Miyamoto et al.

(10) Patent No.: US 9,289,496 B2
(45) Date of Patent: Mar. 22, 2016

(54) LIPID DIPEPTIDE AND GEL

(71) Applicant: Nissan Chemical Industries, Ltd., Tokyo (JP)

(72) Inventors: Misao Miyamoto, Tokyo (JP);
Nobuhide Miyachi, Tokyo (JP);
Takehisa Iwama, Tokyo (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 13/911,500

(22) Filed: Jun. 6, 2013

(65) Prior Publication Data
US 2013/0267609 A1 Oct. 10, 2013

Related U.S. Application Data

(62) Division of application No. 13/056,517, filed as application No. PCT/JP2009/061248 on Jun. 19, 2009.

(30) Foreign Application Priority Data

Aug. 1, 2008 (JP) ................................. 2008-200108

(51) Int. Cl.
| *A61K 38/00* | (2006.01) |
| *A61P 17/00* | (2006.01) |
| *A61K 47/22* | (2006.01) |
| *A61K 9/00* | (2006.01) |
| *A61K 9/70* | (2006.01) |
| *A61K 47/10* | (2006.01) |
| *A61K 47/18* | (2006.01) |
| *C07K 5/062* | (2006.01) |
| *C07K 5/078* | (2006.01) |
| *C07K 5/103* | (2006.01) |

(52) U.S. Cl.
CPC .............. *A61K 47/22* (2013.01); *A61K 9/0014* (2013.01); *A61K 9/7007* (2013.01); *A61K 47/10* (2013.01); *A61K 47/183* (2013.01); *C07K 5/06026* (2013.01); *C07K 5/06052* (2013.01); *C07K 5/06139* (2013.01); *C07K 5/06147* (2013.01); *C07K 5/1008* (2013.01)

(58) Field of Classification Search
None
See application file for complete search history.

(56) References Cited

U.S. PATENT DOCUMENTS

| 4,362,716 | A | 12/1982 | Bouchaudon et al. |
| 5,503,776 | A | 4/1996 | Murase et al. |
| 7,488,841 | B2 | 2/2009 | Yamawaki et al. |
| 2004/0106172 | A1 | 6/2004 | Nakanishi et al. |
| 2005/0142092 | A1 | 6/2005 | Lintner |
| 2005/0265951 | A1 | 12/2005 | Yamawaki et al. |
| 2009/0093388 | A1 | 4/2009 | Yamawaki et al. |
| 2011/0045036 | A1 | 2/2011 | Lintner et al. |

FOREIGN PATENT DOCUMENTS

| EP | 1 547 998 A1 | 6/2005 |
| JP | B2-01-059277 | 12/1989 |
| JP | A-2002-085957 | 3/2002 |
| JP | A-2003-238387 | 8/2003 |
| JP | A-2003-327949 | 11/2003 |
| JP | A-2004-081107 | 3/2004 |
| JP | A-2004-250797 | 9/2004 |
| TW | 200413283 A | 8/2004 |
| WO | WO 2008/089602 A1 | 7/2008 |
| WO | WO 2009/005152 A1 | 1/2009 |

OTHER PUBLICATIONS

Personal Care Magazine, Aloe Vera Acts as Barrier Against Pollutants, Mar. 2008, downloaded on Jun. 4, 2014 from URL: <www.personalcaremagazine.com/Print.aspx?Story =3565>).*
Baldwin (downloaded on Jun. 4, 2014 from URL: <www.herballegacy.com/Baldwin_Chemical.html>).*
Nov. 27, 2012 Office Action issued in Chinese Patent Application No. 200980129362.8 (with translation).
Petka et al., "Reversible hydrogels from self-assembling artificial proteins," Science, Jul. 17, 1998, pp. 389-392, vol. 281.
Aggeli et al., "Self-assembling peptide polyelectrolyte β-sheet complexes form nematic hydrogels," Angew Chemistry Int. Ed., 2003, pp. 5603-5606, vol. 42.
Hartgerink et al., "Self-assembly and mineralization of peptide-amphiphile nanofibers," Science, Nov. 23, 2001, pp. 1684-1688, vol. 294.
Matsumoto et al., "The supramolecular hydrogel toward the 'smart biomaterials'," Dojin News, 2006, pp. 1-16, No. 118.
Yang et al., "Conjugates of naphthalene and dipeptides produce molecular hydrogelators with high efficiency of hydrogelation and superhelical nanofibers," Journal of Materials Chemistry, 2007, pp. 850-854, vol. 17.
Vemula et al., "In situ synthesis of gold nanoparticles using molecular gels and liquid crystals from vitamin-c amphiphiles," Chem. Mat., Dec. 22, 2006, pp. 138-140, vol. 19, American Chemical Society.
Vemula et al., "Smart amphiphiles: hydro/organogelators for in situ reduction of gold," Chem. Comm., 2006, pp. 2218-2220, The Royal Society of Chemistry.
Matsuzawa et al., "Assembly and photoinduced organization of mono- and oligopeptide molecules containing an azobenzene moiety," Advanced Functional Materials, 2007, vol. 17, pp. 1507-1514, Wiley InterScience.
Koda et al., Abstract Paper of the 44th Joint Meeting on Chemistry, Jul. 7, 2007, abstract.

(Continued)

*Primary Examiner* — Karlheinz R Skowronek
*Assistant Examiner* — Sergio Coffa
(74) *Attorney, Agent, or Firm* — Oliff PLC

(57) ABSTRACT

There is provided a gelator that is capable of forming a gel by an extremely small amount of addition in a wide pH range from acidic to alkaline regions, and a gel having high environmental compatibility, biocompatibility, and biodegradability. A gelator comprising: a lipid peptide of Formula (1) wherein $R^1$ is a $C_{9-23}$ aliphatic group, $R^2$ is a hydrogen atom or a $C_{1-4}$ alkyl group optionally having a $C_{1-2}$ branched chain, $R^3$ is a —$(CH_2)_n$—X group, n is a number from 1 to 4, and X is an amino group, a guanidino group, a —$CONH_2$ group, or a 5-membered ring optionally having 1 to 3 nitrogen atoms, a 6-membered ring optionally having 1 to 3 nitrogen atoms, or a fused heterocycle including a 5-membered ring and a 6-membered ring that optionally has 1 to 3 nitrogen atoms); or a pharmaceutically usable salt of the lipid peptide.

12 Claims, 2 Drawing Sheets

(56) References Cited

OTHER PUBLICATIONS

Ohkubo et al., Enantioselectivity enhancement in the deacylation of n-acyl amino acid esters by vesicular systems of long chain dipeptide nucleophiles and a cationic double chain surfactant, *Bull. Chem. Soc. Jpn.*, 1984, pp. 214-218, vol. 57, No. 1.

Fieser et al., "Synthetic emulsifying agents," Harvard University, Jun. 20, 1956, pp. 2825-2832, vol. 78, American Chemical Society.

Kar et al., "Organogelation and hydrogelation of low-molecular-weight amphiphilic dipeptides: pH responsiveness in phase-selective gelation and dye removal," *Langmuir Article*, 2009, pp. 8639-8648, vol. 25, No. 15, American Chemical Society.

Ohkubo et al., "Efficient stereoselective hydrolysis of enantiomeric amino acid esters by bilayer vesicular systems which include di- or tri-peptide histidine catalysts," *J. Chem. Soc.*, 1987, pp. 995-1001, Kumamoto University.

Matsumoto et al., "Studies on thermodynamics for hydrolysis isokinetic temperature related to molecular location of reactants in coaggregates," J.of Org. Chem., 1990, vol. 55, pp. 5797-5799, American Chemical Society.

International Search Report issued in International Patent Application No. PCT/JP2009/061248 dated Aug. 25, 2009.

Kar et al, Organogelation and hydrogelation of low-molecular-weight amphiphillic dipeptides: pH responsiveness in phase-selective gelation and dye removal, Langmuir. Aug. 4, 2009; 25 (15): 8639-8648.

Lupo, Antioxidants and vitamins in cosmetics, Clin Dermatol, Jul.-Aug. 2001; 19 (4): 467-473.

Oct. 2, 2012 Office Action issued in U.S. Appl. No. 13/056,517.

Apr. 24, 2013 Office Action issued in U.S. Appl. No. 13/056,517.

Dec. 19, 2013 Office Action issued in U.S. Appl. No. 13/911,533.

Office Action dated Jul. 17, 2014 issued in U.S. Appl. No. 13/056,517.

Bonacucina et al., "Characterization and Stability of Emulsion Gels Based on Acrylamide/Sodium Acryloyldimethyl Taurate Copolymer," AAPS PharmSciTech, Jun. 2009, pp. 368-375, vol. 10, No. 2.

Jul. 3, 2014 Office Action issued in U.S. Appl. No. 13/911,533.

Mar. 26, 2015 Office Action issued in U.S. Appl. No. 13/056,517.

Gilead et al., "Self-Organization of Short Peptide Fragments: From Amyloid Fibrils to Nanoscale Supramolecular Assemblies," Supramolecular Chemistry, vol. 17 (1-2), pp. 87-92, Jan.-Mar. 2005.

Aug. 14, 2015 Office Action issued in U.S. Appl. No. 13/911,533.

* cited by examiner (a) BEFORE HEATING    (b) AFTER HEATING WITH PAL-GH    (c) AFTER HEATING WITHOUT PAL-GH

LIPID DIPEPTIDE AND GEL

This is a Continuation of application Ser. No. 13/056,517 filed Jan. 28, 2011, which is a National Phase of International Patent Application No. PCT/JP2009/061248 filed Jun. 19, 2009. The disclosure of the prior applications is hereby incorporated by reference herein in its entirety.

TECHNICAL FIELD

The present invention relates to a gelator including a lipid dipeptide, a fiber formed by self-assembly of the gelator, a gel and a gel sheet composed of the gelator or the fiber and various solutions, and a novel lipid dipeptide usable for them.

The lipid peptide of the present invention is particularly suitably used as a gelator in the production of various gel bases for cosmetics, gel foods such as agar, pharmaceutical products, and the like. Furthermore, a gel obtained from the lipid peptide is suitable for commodity applications such as cosmetics, (soft) contact lenses, disposable diapers, and air fresheners, dryland farming applications, analytical chemistry applications such as chromatography, medical and pharmaceutical applications, biochemical field applications such as protein carriers, cell culture related base materials, and bioreactors, and various functional materials.

BACKGROUND ART

A hydrogel is useful as a gel having high biocompatibility because it includes water as a medium, and thus is used in wide fields including commodities such as disposable diapers, cosmetics, and air fresheners.

Examples of a conventional hydrogel include natural polymer gels such as agarose and synthetic polymer gels that are formed by cross-linking chains of a polymer such as an acrylamide gel through chemical covalent bonds.

Recently, functional gels in which various functions such as substance holding capacities, external stimulus responsive performance, and biodegradability in consideration of the environment are imparted to a hydrogel have been attracting much attention, and there are attempts for providing various functions by incorporating functional molecules into the natural or the synthetic polymer gels using copolymerization reaction.

In order to impart a new function to a hydrogel, it is required to study the nanostructure and the surface structure of the gel in detail. However, the method of incorporating a functional molecule using the copolymerization reaction has various problems that the introduction rate of a functional group is limited, that precise molecular design is difficult, that unreacted residual substances have safety issues, and that gel preparation is extremely complicated.

In order to prepare a safe and stable sheet-shaped gel (so-called a gel sheet) without unreacted residual crosslinking agents using such hydrogels, a solution dissolving a natural polymer is placed in a sheet-shape mold and a gel sheet is formed by gelation. However, physical cross-linkages between natural polymers are fragile and in an equilibrium state. Thus, when the gel sheet is immersed in water, the natural polymer is gradually fallen out from the gel sheet into water to disintegrate the gel sheet. In this manner, it has been extremely difficult to prepare a gel sheet only by a physical gel (Non-patent Document 1).

In contrast to such conventional "top-down type" developments of functional materials, "bottom-up type" studies for producing functional materials, in which atoms or molecules as a minimum unit of substances are assembled to form an assembly and a new function is found in a supermolecule as the formed assembly, have been drawing attention.

Also in the field of gels, a new gel composed of a noncovalent gel fiber (so-called "nanofiber self-assembly") has been developed by self-assembly of low molecular compounds. The "self-assembly" means that, in a substance (molecule) group in a random state at first, molecules are spontaneously assembled under suitable external conditions through intermolecular noncovalent interactions and the like to grow to a macro functional assembly.

The new gel draws attention because macroscopic structures or functions of the gel can be theoretically controlled by controlling intermolecular interactions or weak noncovalent bonds of a molecular assembly depending on molecular design of monomers.

However, there is no definite method for controlling the intermolecular interactions or the noncovalent bonds between low-molecular weight compounds. Furthermore, in the studies of the noncovalent gel, the study of self-assembly using hydrogen bonds in an organic solvent is preceded because the gel is comparatively easily formed, and self-assembled compounds in an aqueous solution (that is, a hydrogelator and the like) have been found only incidentally.

Previously reported hydrogelators forming noncovalent gels are generally classified into the following three types.

[1. Hydrogelators Having Amphiphilic Low-Molecular Weight Molecule as Skeleton]

This type of hydrogelators is modeled on an artificial lipid membrane. Examples of the hydrogelator include surfactant gelators having a quaternary ammonium salt part as the hydrophilic portion and an alkyl long chain as the hydrophobic portion and twin-surfactant gelators in which hydrophilic portions of two surfactant molecules are connected.

As an example of the hydrogel produced by such gelators, there has been developed a molecular organizational hydrogel formed by adding an anionic compound having a molecular weight of 90 or more to an aqueous solution dispersing a cationic amphiphilic compound having a branched alkyl group as the hydrophobic portion (Patent Document 1).

[2. Hydrogelators Having Skeleton in Motif of Biocomponents]

Examples of the hydrogelator include gelators using assembly between molecular assemblies by a peptide secondary structure skeleton (such as an α-helix structure and a β-sheet structure).

For example, there has been developed a gelator having an α-helix structure (Non-patent Document 2) and a gelator having a β-sheet structure (Non-patent Document 3).

[3. Hydrogelators Having Semi-Artificial Low-Molecular Weight Molecule as Skeleton]

This type of hydrogelators is composed of a combination of a biocomponent such as DNA bases, peptide chains, and sugar chains (hydrophilic portion), an alkyl chain (hydrophobic portion), and the like, and can be considered as a gelator in which the characteristics of the above two types of gelators are combined. Here, the DNA bases, the peptide chains, and the sugar chains have roles not only for improving hydrophilicity but also for imparting intermolecular interactions such as a hydrogen bond.

For example, there has been developed a hydrogelator composed of a glycoside-amino acid derivative including a sugar structure moiety having a glycoside structure of N-acetylated monosaccharides or disaccharides (Patent Document 2) and a fine hollow fiber composed of a peptide lipid of General Formula "$RCO(NHCH_2CO)_mOH$" and a transition-metal and having self-assembling property (Patent Document 3).

There is also disclosed a formation of β-sheet fiber network from an amphiphilic peptide having a structure of <hydrophobic portion-cysteine residue (forming disulfide bonds at the time of network formation)-glycine residue (imparting flexibility)-phosphorylated serine residue-cell adhesive peptide> using the hydrophobic portion as a core (Non-patent Document 4).

There has been reported preparation of a glycolipid supermolecular hydrogel using a chemical library (Non-patent Document 5).

Amphiphilic dipeptide compounds composed of a hydrophobic portion and a dipeptide are also drawing attention as one of the "bottom-up type" functional materials capable of forming a self-assembly. For example, it is known that a dipeptide compound having a specific lipid part of "2-(naphthalen-2-yloxy)acetic acid" and "glycylglycine, glycylserine, or the like" can form a hydrogel. However, such compounds can form a gel from only an acidic aqueous solution or a hydrogel formed from each is acidic (Non-patent Document 6).

Furthermore, few of the low-molecular weight hydrogels that have been thus developed can form a gel not only from an aqueous solution but also from an organic solvent, and hydrogels capable of forming a gel from both of the solvents have a limited structure. Even hydrogels capable of forming a gel from both of the solvents can form a gel only from a combination of water or an aqueous solution having a limited pH and a specific organic solvent (Non-patent Documents 7 to 9). That is, there are no gelators that can form a gel from an aqueous solution in a wide pH range as well as have gelation properties with respect to an organic solvent including solvents practically used for cosmetics and the like.

In contrast, a lipid peptide compound composed of lauric acid or myristic acid that is a natural fatty acid and glycylglycine does not form a hydrogel but forms an organic nanotube including multilayered vesicles of a hollow having an inner diameter of about 50 to 90 nm to be precipitated (for example, Patent Document 3). On the other hand, it has been found that palmitoyl-Gly-Gly-His that is formed by adding histidine to the C-terminal of glycylglycine and bonding palmitic acid as a natural fatty acid to the N-terminal has gelation properties. Moreover, it has been reported that palmitoyl-Gly-Gly-Gly-His that is formed by bonding palmitic acid to a tetrapeptide in place of the tripeptide has high gelation properties at a lowest gelation concentration of only 0.03 wt % (Non-patent Document 10).

In this manner, it is supposed that when the hydrophilic portion has a longer peptide chain, the number of hydrogen bonds between lipid peptides increases, and thus a stably assembled lipid peptide can be obtained. However, it is unknown until now whether a lipid peptide compound is self-assembled to form a gel when the hydrophilic portion has a shorter peptide chain and thus the number of hydrogen bonds between lipid peptides decreases.

Furthermore, even by the palmitoyl-Gly-Gly-Gly-His, it has been reported until now that a gel can be formed only from a few mediums such as 1 N hydrochloric acid aqueous solution, neutral and basic aqueous solutions, and a mixed solution of ethanol and water, and there are no reports on gelation using various acids or inorganic salts and on gelation of organic solvents used for cosmetics and external medicines.

RELATED ART DOCUMENTS

Patent Document

Patent Document 1: Japanese Patent Application Publication No. JP-A-2002-085957.

Patent Document 2: Japanese Patent Application Publication No. JP-A-2003-327949.

Patent Document 3: Japanese Patent Application Publication No. JP-A-2004-250797.

Non-Patent Document

Non-patent Document 1: Katsuyoshi Nishinari, K. S. Hossain, Shimon Tanaka, Yoko Nitta, Makoto Takemasa, Fang Yapeng, Toyoichi Tanaka Memorial Symposium, The Discovery of Volume Phase Transition of Gel—the Following 30 Years, the abstract paper, Sep. 10-12, 2008, SS-1, p. 39.

Non-patent Document 2: W. A. Pekata et al., SCIENCE, 281, 389 (1998).

Non-patent Document 3: A. Aggeli et al., Angew. Chem. Int. Ed., 2003, 42. 5603-5606.

Non-patent Document 4: Jeffry D. Hartgerink, Elia Beniaah, Samuel I. Stupp, SCIENCE, vol 294, 1684-1688 (2001).

Non-patent Document 5: Shinji Matsumoto, Itaru Hamachi, Jojin News, No. 118, 1-16 (2006).

Non-patent Document 6: Z. Yang, B. Xu et al., J. Mater. Chem., 2007, 17, 850-854.

Non-patent Document 7: P. K. Kumar et al., Chem. Mater., 2007, 19, 138-140.

Non-patent Document 8: P. K. Kumar and G. John, Chem. Commun., 2006, 2218-2220.

Non-patent Document 9: Y. Matsuzawa, M. Abe et al., Adv. Funct. Mater., 2007, 17, 1507-1514.

Non-patent Document 10: Daisuke Koda, Tatsuo Maruyama, Saori Sonokawa, Kazuki Nakajima, Masahiro Goto, The 44th Joint Meeting on Chemistry in Kyushu, Jul. 7, 2007, the abstract paper.

DISCLOSURE OF THE INVENTION

Problem to be Solved by the Invention

In conventional hydrogels, when a synthetic polymer gel is formed, or sometimes when a gel is formed from a natural polymer such as gelatin (collagen), a crosslinking agent having an aldehyde group is required to be used.

Furthermore, in order to impart a function to a natural polymer gel as well as a (synthetic) polymer gel, chemical modification of the polymer chain or copolymerization reaction is required for incorporating a functional molecule.

In this manner, conventional hydrogels have problems that gel preparation is complicated and that unreacted crosslinking agents or unreacted substances during copolymerization reaction remain in the gel.

Furthermore, among previously developed hydrogelators forming noncovalent gels, the hydrogelator having the amphiphilic low-molecular weight molecule as the skeleton (1) may not form a gel depending on the pH of a medium. That is, in an alkaline region, the hydrogelator forms micelles to become an emulsion. In contrast, in an acidic region, the hydrogelator is fibrously self-assembled to form a hydrogel. However, in a neutral region that is considered to be safe for living bodies, there are few reports on hydrogelation. Furthermore, there is a problem that quaternary ammonium cations and the like (for example Patent Document 1) may have safety issues in a biological environment.

The hydrogelator having a skeleton in the motif of biocomponents (2) has a problem of productivity, that is, unsuitable for mass production, and a problem that the gel forming ability varies depending on temperature or pH.

The hydrogelator having a semi-artificial low-molecular weight molecule as the skeleton (3) also has problems in biocompatibility and environmental safety. For example, according to Patent Document 2, the use of high toxic sodium azide is shown in a reaction scheme (FIG. 1) for synthesizing a glycoside-amino acid derivative composing the hydrogelator. According to Patent Document 3, a transition-metal (ion) is required to be added for self-assembling the hollow fiber.

In this manner, in previously reported various noncovalent hydrogels and hydrogelators for forming the gels, there is a demand for further improvement of the gel forming ability (gel structure holding ability) and the safety in a biological environment.

From the viewpoint of the safety in a biological environment, there is a potential demand of a hydrogelator capable of forming a gel by a smaller amount of addition.

For developing such hydrogelators, an amino acid having three or four or more of peptide units is required when a lipid peptide having high gel forming ability is developed using a combination of a natural fatty acid and the amino acid, and thus the producing process and the like become complicated. Therefore, there is a demand to provide a compound having a simpler structure and capable of being produced in a short process and in an industrial scale.

Furthermore, from the viewpoint of wide applications for medical and agrochemical preparations, cosmetics, ink, paint, and the like, there is a demand to provide a gelator capable of forming a gel not only from water and an aqueous medium but also from various solutions and solutions having a wide pH range as well as a mixed solution of water and an organic solvent and a hydrophobic organic solution.

Furthermore, in the case of preparation of a sheet-shaped gel, that is, a gel sheet, even when a physical gel is used to prepare a safe gel sheet without a chemical crosslinking agent, a stable gel sheet that is not disintegrated even when it is immersed in water cannot be prepared. There is a demand to provide such safety and stable gel sheet because the gel sheet has moisturizing effect on skin and the like and has wide applications for a moisturizing agent for skin, a wound dressing, a face pack, and a sustained-release carrier for medical and agrochemical preparations.

In view of the above-described circumstances, it is an object of the present invention to provide a gelator including a novel lipid peptide, in particular, a lipid peptide having high gelation properties capable of forming a gel by an extremely small amount of addition from a mixed solution of an alcohol, an organic solvent, and the like or a solution dissolving an organic acid, an inorganic acid, an inorganic salt, or an organic salt, in a wide pH range from acidic to alkaline regions, specifically even in a neutral region.

The present invention also has an object to provide a gel that is obtained by using the gelator including the lipid peptide, that keeps a stable gel structure in a wide pH range from acidic to alkaline regions, and that has high environmental compatibility, biocompatibility, and biodegradability.

The present invention has an object to provide a gelator and a gel capable of forming a safety and stable sheet-shaped gel (so-called a gel sheet) only by physical cross-linkages without a crosslinking agent.

The present invention has a further object to provide a gel that is formed by adsorption or inclusion of a low-molecular weight compound to a fiber formed by self-assembling the gelator including the lipid peptide and that can be used as base materials for medical and agrochemical preparations capable of sustained-releasing the low-molecular weight compound.

The present invention also has an object to provide a novel lipid peptide capable of providing the gelation properties and the gel.

Means for Solving the Problem

The inventors of the present invention have carried out intensive studies in order to solve the problems, and as a result, have found the present invention. That is, as a first aspect, a gelator is characterized by including a lipid peptide of Formula (1):

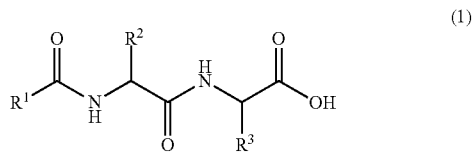

(where $R^1$ is a $C_{9-23}$ aliphatic group, $R^2$ is a hydrogen atom or a $C_{1-4}$ alkyl group optionally having a $C_{1-2}$ branched chain, $R^3$ is a —$(CH_2)_n$—X group, n is a number from 1 to 4, and X is an amino group, a guanidino group, a —$CONH_2$ group, or a 5-membered ring optionally having 1 to 3 nitrogen atoms, a 6-membered ring optionally having 1 to 3 nitrogen atoms, or a fused heterocycle including a 5-membered ring and a 6-membered ring that optionally has 1 to 3 nitrogen atoms) or a pharmaceutically usable salt of the lipid peptide.

As a second aspect, in the gelator according to the first aspect, $R^3$ is a —$(CH_2)_n$—X group, n is a number from 1 to 4, and X is an amino group, a guanidino group, a —$CONH_2$ group, or a 5-membered ring optionally having 1 to 2 nitrogen atoms or a fused heterocycle including a 5-membered ring and a 6-membered ring that optionally has 1 to 2 nitrogen atoms.

As a third aspect, in the gelator according to the first aspect or the second aspect, $R^1$ is a $C_{11-21}$ straight chain aliphatic group optionally having 0 to 2 unsaturated bonds.

As a fourth aspect, in the gelator according to the third aspect, $R^2$ is a hydrogen atom or a $C_{1-3}$ alkyl group optionally having a $C_1$ branched chain.

As a fifth aspect, in the gelator according to the fourth aspect, n is a number from 1 to 4 and X is an amino group, a guanidino group, or a —$CONH_2$ group, or n is 1 and X is a pyrrole group, an imidazole group, a pyrazole group, or an imidazole group.

As a sixth aspect, in the gelator according to the fifth aspect, $R^2$ is a hydrogen atom, a methyl group, an ethyl group, a n-propyl group, an isopropyl group, a n-butyl group, an isobutyl group, a sec-butyl group, or a tert-butyl group, and $R^3$ is an aminomethyl group, an aminoethyl group, a 3-aminopropyl group, a 4-aminobutyl group, a carbamoylmethyl group, a 2-carbamoylethyl group, a 3-carbamoylbutyl group, a 2-guanidinoethyl group, a 3-guanidinobutyl group, a pyrrole methyl group, an imidazole methyl group, a pyrazole methyl group, or a 3-indole methyl group.

As a seventh aspect, in the gelator according to the sixth aspect, $R^2$ is a hydrogen atom, a methyl group, an isopropyl group, an isobutyl group, or a sec-butyl group, and $R^3$ is a 4-aminobutyl group, a carbamoylmethyl group, a 2-carbamoylethyl group, a 3-guanidinobutyl group, an imidazole methyl group, or a 3-indole methyl group.

As an eighth aspect, a fiber is formed by self-assembly of the gelator as described in any one of the first aspect to the seventh aspect.

As a ninth aspect, a fiber is formed by self-assembly of a mixture of the gelator as described in any one of the first aspect to the seventh aspect and a gelator including a lipid peptide of Formula (2):

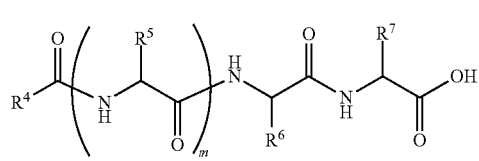

(where $R^4$ is a $C_{9-23}$ aliphatic group, each of $R^5$, $R^6$, and $R^7$ is a hydrogen atom, a $C_{1-4}$ alkyl chain optionally having a $C_{1-2}$ branched chain, or —$(CH_2)_n$—X and at least one or more of $R^5$, $R^6$, and $R^7$ is —$(CH_2)_n$—X, n is a number from 1 to 4, X is an amino group, a guanidino group, a —$CONH_2$ group, or a 5-membered ring optionally having 1 to 3 nitrogen atoms, a 6-membered ring optionally having 1 to 3 nitrogen atoms, or a fused heterocycle including a 5-membered ring and a 6-membered ring that optionally has 1 to 3 nitrogen atoms, and m is a number from 1 to 4) or a pharmacologically usable salt of the lipid peptide.

As a tenth aspect, in the fiber according to the eighth aspect or the ninth aspect, the self-assembly is accelerated by addition of a surfactant.

As an eleventh aspect, in the fiber according to the tenth aspect, the surfactant is an anionic surfactant, a nonionic surfactant, or a cationic surfactant.

As a twelfth aspect, a gel includes the gelator as claimed in any one of the first aspect to the seventh aspect and a solvent.

As a thirteenth aspect, a gel includes the fiber as claimed in any one of the eighth aspect to the eleventh aspect and a solvent.

As a fourteenth aspect, in the gel according to the thirteenth aspect, the fiber adheres to or includes a low-molecular weight compound.

As a fifteenth aspect, in the gel according to the twelfth aspect or the thirteenth aspect, the solvent is water, an alcohol, an aqueous solution, an alcoholic solution, a hydrophilic organic solution, a higher alcohol, a fatty acid, higher fatty acid esters, a glyceride, a hydrophobic organic solution, or a miscible mixed solvent thereof.

As a sixteenth aspect, in the gel according to the fifteenth aspect, the solvent is water, an alcohol, an aqueous solution, an alcoholic solution, a hydrophilic organic solution, a higher alcohol, a hydrophobic organic solution, or a miscible mixed solvent thereof.

As a seventeenth aspect, in the gel according to the fifteenth aspect, the alcoholic solution is a mixed solution of at least one alcohol selected from a group consisting of methanol, ethanol, 2-propanol, and i-butanol and water.

As an eighteenth aspect, in the gel according to the fifteenth aspect, the hydrophilic organic solution is a mixed solution of at least one hydrophilic organic solvent selected from a group consisting of acetone, dioxane, glycerin, propylene glycol, and polyethylene glycol and water.

As a nineteenth aspect, in the gel according to the fifteenth aspect, the hydrophobic organic solution is a solution of at least one hydrophobic organic solvent selected from a group consisting of a liquid paraffin, a mineral oil, hydrogenated polyisobutene, and olive oil.

As a twentieth aspect, in the gel according to the fifteenth aspect, the aqueous solution is an aqueous solution dissolving at least one inorganic salt selected from a group consisting of an inorganic carbonate, an inorganic sulfate, an inorganic phosphate, and an inorganic hydrogen phosphate or at least one organic salt selected from a group consisting of an organic amine hydrochloride and an organic amine acetate.

As a twenty-first aspect, in the gel according to the twentieth aspect, the inorganic salt is at least one inorganic salt selected from a group consisting of calcium carbonate, sodium carbonate, potassium carbonate, sodium sulfate, potassium sulfate, magnesium sulfate, potassium phosphate, sodium phosphate, disodium hydrogen phosphate, and sodium dihydrogen phosphate, and the organic salt is at least one organic salt selected from a group consisting of ethylenediamine hydrochloride, ethylenediaminetetraacetate, and trishydroxymethylaminomethane hydrochloride.

As a twenty-second aspect, the gel according to any one of the twelfth aspect to the twenty-first aspect further includes an antiseptic.

As a twenty-third aspect, the gel according to any one of the twelfth aspect to the twenty-second aspect in which the gel is a sheet-shaped gel.

As a twenty-fourth aspect, a film is obtained by evaporation of a solvent from the sheet-shaped gel according to the twenty-third aspect.

As a twenty-fifth aspect, a lipid peptide of Formula (1b):

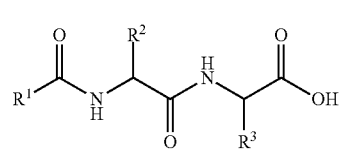

(where $R^1$ is a $C_{12-22}$ aliphatic group, $R^2$ is a hydrogen atom, and $R^3$ is a 3-indole methyl group or an imidazole methyl group) and a pharmaceutically usable salt of the lipid peptide are provided.

As a twenty-sixth aspect, a lipid peptide of Formula (1c):

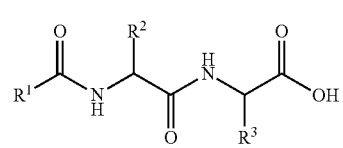

(where $R^1$ is a $C_{14-22}$ aliphatic group, $R^2$ is a hydrogen atom, a methyl group, an isopropyl group, an isobutyl group, or a 2-butyl group, and $R^3$ is a 4-amino-n-butyl group, a carbamoylethyl group, a carbamoylmethyl group, an imidazole methyl group, or a 3-indole methyl group) and a pharmaceutically usable salt of the lipid peptide are provided.

As a twenty-seventh aspect, in the lipid peptide and the pharmaceutically usable salt of the lipid peptide according to the twenty-sixth aspect, $R^2$ is a methyl group, an isopropyl group, an isobutyl group, or a 2-butyl group, and $R^3$ is a 4-amino-n-butyl group, a carbamoylethyl group, or a carbamoylmethyl group.

As a twenty-eighth aspect, in the lipid peptide and the pharmaceutically usable salt of the lipid peptide according to the twenty-sixth aspect, $R^2$ is a methyl group, an isopropyl group, an isobutyl group, or a 2-butyl group, and $R^3$ is an imidazole methyl group or a 3-indole methyl group.

As a twenty-ninth aspect, in the lipid peptide and the pharmaceutically usable salt of the lipid peptide according to the twenty-sixth aspect, $R^2$ is a hydrogen atom, and $R^3$ is a 4-amino-n-butyl group, a carbamoylethyl group, or a carbamoylmethyl group.

As a thirtieth aspect, a gelator is characterized by including a lipid peptide of Formula (3):

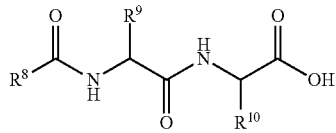

(3)

(where $R^8$ is a $C_{9-23}$ aliphatic group, $R^9$ is a —$(CH_2)_n$—X group, $R^{10}$ is a hydrogen atom or a $C_{1-4}$ alkyl group optionally having a $C_{1-2}$ branched chain, n is a number from 1 to 4, and X is an amino group, a guanidino group, a —$CONH_2$ group, or a 5-membered ring optionally having 1 to 3 nitrogen atoms, a 6-membered ring optionally having 1 to 3 nitrogen atoms, or a fused heterocycle including a 5-membered ring and a 6-membered ring that optionally has 1 to 3 nitrogen atoms), or a pharmaceutically usable salt of the lipid peptide.

As a thirty-first aspect, a lipid peptide of Formula (3):

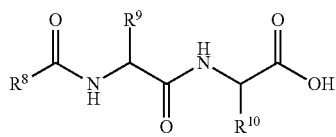

(3)

(where $R^8$ is a $C_{9-23}$ aliphatic group, $R^9$ is a —$(CH_2)_n$—X group, $R^{10}$ is a hydrogen atom or a $C_{1-4}$ alkyl group optionally having a $C_{1-2}$ branched chain, n is a number from 1 to 4, and X is an amino group, a guanidino group, a —$CONH_2$ group, or a 5-membered ring optionally having 1 to 3 nitrogen atoms, a 6-membered ring optionally having 1 to 3 nitrogen atoms, or a fused heterocycle including a 5-membered ring and a 6-membered ring that optionally has 1 to 3 nitrogen atoms) and a pharmaceutically usable salt of the lipid peptide are provided.

Effect of the Invention

The gelator of the present invention can form a gel from an aqueous solution or an alcoholic aqueous solution by gelation without a crosslinking agent or the like that is required for conventional gel formation, and thus an unreacted crosslinking agent does not remain. Furthermore, the lipid peptide of the present invention is composed of a low-molecular weight compound, and thus can form a gel without containing unreacted substances of functional molecules, which are incorporated for providing functions in conventional gelators.

Furthermore, the gelator of the present invention can form a gel in a wide pH range from an acidic region to an alkaline region. In particular, from the viewpoint of high safety that is required in carriers for cell culture, medical materials, cosmetic materials, and the like, the lipid peptide of the present invention having gel forming ability even in a neutral region is useful as a gelator for the applications.

Furthermore, in the gelator of the present invention, the lipid peptide of the present invention can form a gel not only from water but also from various solvents such as an alcohol, an aqueous solution, an alcoholic solution, a hydrophilic organic solution, a higher alcohol, a fatty acid, higher fatty acid esters, a glyceride, and a hydrophobic organic solution as well as a miscible mixed solvent thereof, and thus the gelator is useful as a gelator for applications such as agrochemical preparations, ink, and paint along with the above applications.

The gelator of the present invention has gel forming ability as a gelator even when two or more of lipid peptides forming the gelator are mixed in the gelator.

Furthermore, even when other various peptides capable of forming a self-assembly, that is, tripeptides or tetrapeptides having the N-terminal modified with a fatty acid in addition to the lipid peptide of Formula (1), are mixed, the gelator of the present invention can form each self-assembly or a mixed self-assembly.

Moreover, even from an aqueous solution dissolving an anionic surfactant, a nonionic surfactant, or a cationic surfactant, the gelator of the present invention can form a self-assembly mixed with the surfactant.

The gelator of the present invention can form a gel capable of sustained-releasing a low-molecular weight compound that is adsorbed to or included in a fiber formed by self-assembly of the gelator.

The gelator of the present invention is a lipid dipeptide derivative composed of a fatty acid and two amino acids alone. In view of conventional arts, in order to obtain a stable gelator, there is a possible method of increasing the number of amino acids composing the peptide derivative. In contrast, the inventors of the present invention have found that even when the number of amino acids is decreased so as to include only two dipeptides, the gelator surprisingly has the gelation properties, and have successfully found a gelator that can be synthesized in a shorter process than that for a conventional hydrogelator and that can be commercialized.

Furthermore, the dipeptide provides a good balance between a hydrophobic moiety and a hydrophilic moiety. Thus, a gel can be formed not only from pure water but also from an aqueous solution containing various acids and/or bases, an alcoholic solvent such as ethanol, and an organic solvent such as glycerin used for cosmetics.

Palmitoyl-Gly-Gly-Gly-His as the conventional art limits usable aqueous mediums. For example, there is a fact that it is insoluble in 50 mM citrate buffer with pH 5, 50 mM acetate buffer with pH 5, and the like even when heated. Furthermore, there is another fact that palmitoyl-Gly-Gly-Gly-His does not form a gel in an ethanol/water mixed solvent having an ethanol concentration of 80% or more.

In contrast, the gelator of the present invention (palmitoyl-Gly-His) can form a gel in a wide variety of mediums including such mediums, and thus mediums can be selected from a much wider range.

The gelator of the present invention does not use animal-derived materials (such as collagen, gelatin, and matrigel) that recently have the issue of BSE infection and the like and uses an artificial low-molecular weight compound (lipid peptide) composed of a lipid and a peptide alone. Thus, the obtained gel has no issue caused by such infection and the like. Moreover, the lipid peptide can be produced only by amidation of a lipid and a peptide without using a toxic reagent with high reactivity such as sodium azide, and thus can suitably be used as a highly safe gelator.

The lipid peptide of the present invention can be used for cellular damage protection and Langmuir monolayer along with the above applications.

The fiber of the present invention is less prone to cause rejection of living cells and has excellent cell-adhesive properties when it is incorporated in a living body because the peptide part (amino acids) is located on the outermost side (that is, the fiber surface) during self-assembly of the lipid peptide in water or an aqueous medium such as an alcohol, an aqueous solution, an alcoholic solution, and a hydrophilic organic solution. On this account, the fiber can preferably be used for sustained-release carriers and adsorbents for medical use, scaffolding materials for regenerative medicine, and the like.

In addition to the above applications, the fiber is useful as stabilizers, dispersants, and wetting agent in food industries, agriculture and forestry, cosmetic fields, and fiber industries, as nano components doped with a metal or an electrically conductive substance in electronics and information fields, and as filter materials and electrically conductive materials.

The gel of the present invention is preferably used as biochemical materials and medical materials for cell culture and the like because it can stably keep a gel structure in a wide pH range from an acidic region to an alkaline region, especially in a neutral condition.

Furthermore, the gel of the present invention is a highly safe gel in both biological and environmental aspects because it can be obtained by addition of a smaller amount of the gelator than conventional agents as described above.

Moreover, as described above, the gel obtained from a lipid peptide as a low-molecular weight compound reduces environmental and biological burdens because it can be readily decomposed by soil bacteria and the like when it is used in an external environment, for example, in soil, and because it can be readily decomposed by metabolic enzymes when it is used in a living body.

The gel of the present invention can produce a solution simultaneously dissolving hydrophilic compounds and hydrophobic compounds because the gelator (lipid peptide) is self-assembled to form a fiber structure and a hydrophobic compound such as vitamin E and methylparaben is incorporated into the fiber to be solubilized. That is, the gel is effectively used for producing cosmetics, quasi-drugs, pharmaceutical products, agrochemical products, and the like when a compound to be solubilized is a physiologically active substance, and is useful for base materials of ink, paint, and the like when a material to be solubilized is a dye or a pigment.

The gel of the present invention is formed by self-assembling the gelator. Thus, a sheet-shaped gel (so-called a gel sheet) obtained by gelation from a solution dissolving the gelator in a sheet-shaped mold becomes a safe and stable gel sheet that includes no chemical cross-linkages and that is not disintegrated even when it is immersed in a solution such as water. That is, such gel sheet has moisturizing effect, can release drugs or can trap harmful compounds, and thus is useful as moisturizing agents, face packs, and base materials for external preparations such as wound dressing.

Moreover, when a solvent in the gel sheet is evaporated without freeze-drying, a film including a lipid peptide as the gelator can be prepared.

BEST MODES FOR CARRYING OUT THE INVENTION

Figure 1:
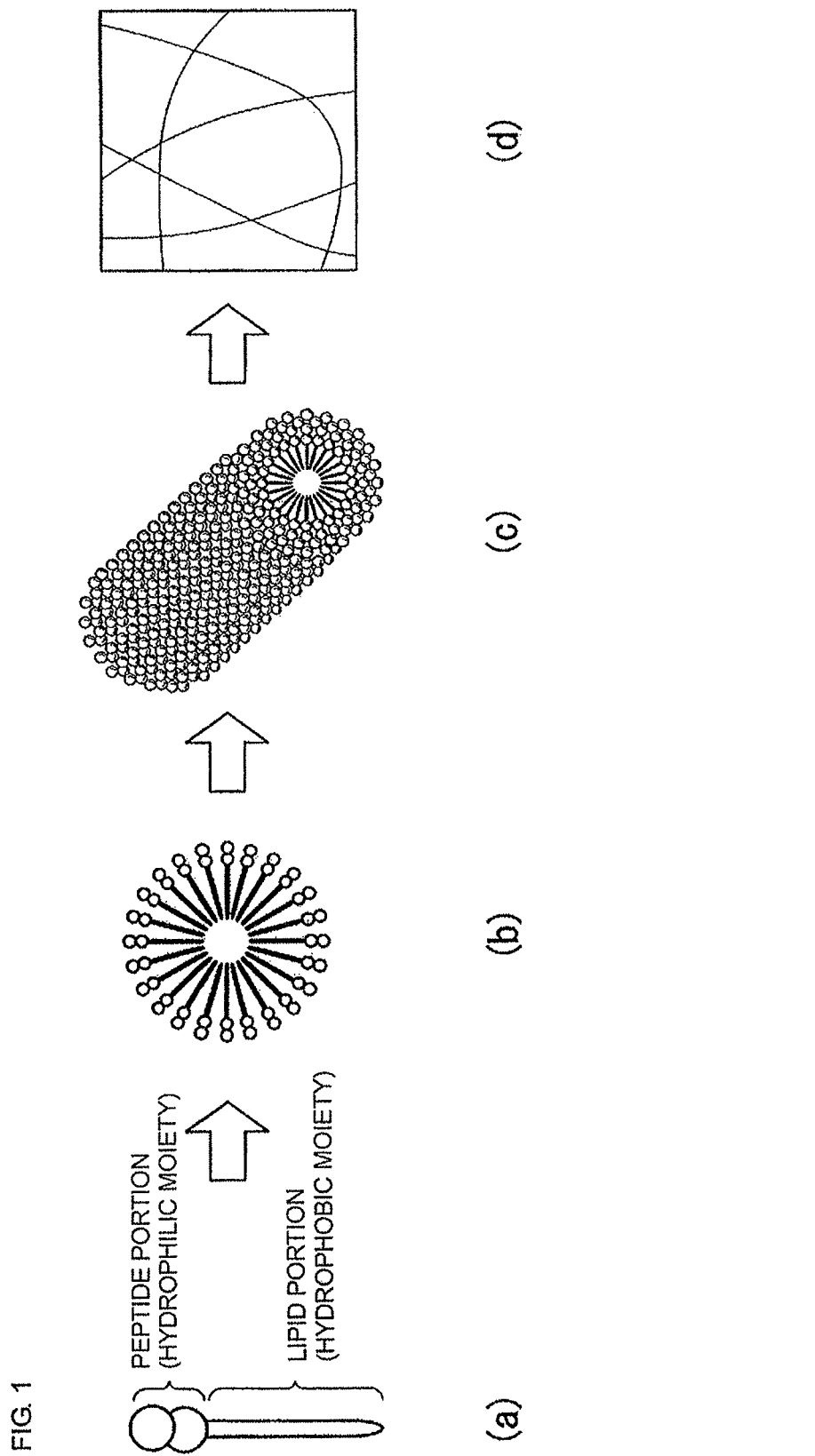
FIG. 1 is a schematic diagram showing self-assembly of lipid peptides and the following gelation.

The present invention will be described in further detail. In the present invention, "n" means normal, "i" means iso, "s" or "sec" means secondary, "t" or "tert" means tertiary, "c" means cyclo, "o" means ortho, "m" means meta, "p" means para, "Me" means a methyl group, "Bu" means a butyl group, and "tBu" means a tertiary butyl group.

[Gelator]

The gelator of the present invention includes a lipid peptide having the structure of (1) below or its pharmaceutically usable salt. The lipid peptide includes a lipid portion (alkylcarbonyl group) having a highly lipophilic chain and a hydrophilic peptide portion (dipeptide).

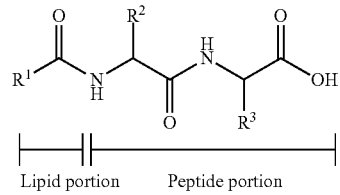

(1)

Lipid portion    Peptide portion

In (1), it is desirable that $R^1$ included in the lipid portion be a $C_{9-23}$ aliphatic group and $R^1$ preferably be a $C_{11-21}$ straight chain aliphatic group or a $C_{11-21}$ straight chain aliphatic group having one or two unsaturated bonds.

Specific examples of the particularly preferable aliphatic group of $R^1$ include a nonyl group, a decyl group (caprylic group), a undecyl group, a dodecyl group (lauryl group), a tridecyl group, a tetradecyl group (myristyl group), a pentadecyl group, a hexadecyl group (palmityl group), a heptadecyl group, an octadecyl group (stearyl group), a nonadecyl group, an icosyl group, and a henicosyl group.

In Formula (1), $R^2$ included in the peptide portion is a hydrogen atom or a $C_{1-4}$ alkyl group optionally having a $C_{1-2}$ branched chain, and $R^3$ is a —$(CH_2)_n$—X group.

In the —$(CH_2)_n$—X group, n is a number from 1 to 4, and X is an amino group, a guanidino group, a —$CONH_2$ group, or a 5-membered ring, a 6-membered ring, or a fused heterocycle including a 5-membered ring and a 6-membered ring optionally having 1 to 3 nitrogen atoms.

The $C_{1-4}$ alkyl group optionally having a $C_{1-2}$ branched chain in $R^2$ means an alkyl group that has a $C_{1-4}$ main chain and may have a $C_{1-2}$ branched chain. Specific examples of the group include a methyl group, an ethyl group, a n-propyl group, an i-propyl group, a n-butyl group, an i-butyl group, a sec-butyl group, and a tert-butyl group.

$R^2$ is preferably a hydrogen atom or a $C_{1-3}$ alkyl group optionally having a $C_1$ branched chain and more preferably a hydrogen atom. The $C_{1-3}$ alkyl group optionally having a $C_1$ branched chain means an alkyl group that has a $C_{1-3}$ main chain and may have a $C_1$ branched chain. Specific examples of the group include a methyl group, an ethyl group, a n-propyl group, an i-propyl group, an i-butyl group, and a sec-butyl group. The group is preferably a methyl group, an i-propyl group, an i-butyl group, or a sec-butyl group.

In the —$(CH_2)_n$— group, X is preferably an amino group, a guanidino group, a —$CONH_2$ group, a pyrrole group, an imidazole group, a pyrazole group, or an indole group and more preferably an imidazole group. Furthermore, in the —$(CH_2)_n$— group, n is preferably 1 or 2 and more preferably 1.

Thus, the —$(CH_2)_n$— group is preferably an aminomethyl group, a 2-aminoethyl group, a 3-aminopropyl group, a 4-aminobutyl group, a carbamoylmethyl group, a 2-carbamoylethyl group, a 3-carbamoylbutyl group, a 2-guanidinoethyl group, a 3-guanidinobutyl group, a pyrrole methyl group, an imidazole methyl group, a pyrazole methyl group, or a 3-indole methyl group, more preferably a 4-aminobutyl group, a carbamoylmethyl group, a 2-carbamoylethyl group, a 3-guanidinobutyl group, an imidazole methyl group, or a 3-indole methyl group, and even more preferably an imidazole methyl group.

Specific examples of the particularly preferable lipid peptide compound of Formula (1) include compounds composed of a lipid portion and a dipeptide portion shown below. Here, the following abbreviations are used for the respective amino acids: histidine (His); glycine (Gly); valine (Val); isoleucine (Ile); alanine (Ala); arginine (Arg); asparagine (Asn); glutamine (Gln); lysine (Lys); and tryptophan (Trp). That is, N-lauroyl-Gly-His, N-lauroyl-Gly-Trp, N-lauroyl-Gly-Gln, N-lauroyl-Gly-Asn, N-lauroyl-Gly-Arg, N-lauroyl-Gly-Lys, N-lauroyl-Ala-His, N-lauroyl-Ala-Trp, N-lauroyl-Ala-Gln, N-lauroyl-Ala-Asn, N-lauroyl-Ala-Arg, N-lauroyl-Ala-Lys, N-lauroyl-Val-His, N-lauroyl-Val-Trp, N-lauroyl-Val-Gln, N-lauroyl-Val-Asn, N-lauroyl-Val-Arg, N-lauroyl-Val-Lys, N-lauroyl-Leu-His, N-lauroyl-Leu-Trp, N-lauroyl-Leu-Gln, N-lauroyl-Leu-Asn, N-lauroyl-Leu-Arg, N-lauroyl-Leu-Lys, N-lauroyl-Ile-His, N-lauroyl-Ile-Trp, N-lauroyl-Ile-Gln, N-lauroyl-Ile-Asn, N-lauroyl-Ile-Arg, N-lauroyl-Ile-Lys, N-myristoyl-Gly-His, N-myristoyl-Gly-Trp, N-myristoyl-Gly-Gln, N-myristoyl-Gly-Asn, N-myristoyl-Gly-Arg, N-myristoyl-Gly-Lys, N-myristoyl-Ala-His, N-myristoyl-Ala-Trp, N-myristoyl-Ala-Gln, N-myristoyl-Ala-Asn, N-myristoyl-Ala-Arg, N-myristoyl-Ala-Lys, N-myristoyl-Val-His, N-myristoyl-Val-Trp, N-myristoyl-Val-Gln, N-myristoyl-Val-Asn, N-myristoyl-Val-Arg, N-myristoyl-Val-Lys, N-myristoyl-Leu-His, N-myristoyl-Leu-Trp, N-myristoyl-Leu-Gln, N-myristoyl-Leu-Asn, N-myristoyl-Leu-Arg, N-myristoyl-Leu-Lys, N-myristoyl-Ile-His, N-myristoyl-Ile-Trp, N-myristoyl-Ile-Gln, N-myristoyl-Ile-Asn, N-myristoyl-Ile-Arg, N-myristoyl-Ile-Lys, N-palmitoyl-Gly-His, N-palmitoyl-Gly-Trp, N-palmitoyl-Gly-Gln, N-palmitoyl-Gly-Asn, N-palmitoyl-Gly-Arg, N-palmitoyl-Gly-Lys, N-palmitoyl-Ala-His, N-palmitoyl-Ala-Trp, N-palmitoyl-Ala-Gln, N-palmitoyl-Ala-Asn, N-palmitoyl-Ala-Arg, N-palmitoyl-Ala-Lys, N-palmitoyl-Val-His, N-palmitoyl-Val-Trp, N-palmitoyl-Val-Gln, N-palmitoyl-Val-Asn, N-palmitoyl-Val-Arg, N-palmitoyl-Val-Lys, N-palmitoyl-Leu-His, N-palmitoyl-Leu-Trp, N-palmitoyl-Leu-Gln, N-palmitoyl-Leu-Asn, N-palmitoyl-Leu-Arg, N-palmitoyl-Leu-Lys, N-palmitoyl-Ile-His, N-palmitoyl-Ile-Trp, N-palmitoyl-Ile-Gln, N-palmitoyl-Ile-Asn, N-palmitoyl-Ile-Arg, N-palmitoyl-Ile-Lys, N-margaroyl-Gly-His, N-margaroyl-Gly-Trp, N-margaroyl-Gly-Gln, N-margaroyl-Gly-Asn, N-margaroyl-Gly-Arg, N-margaroyl-Gly-Lys, N-margaroyl-Ala-His, N-margaroyl-Ala-Trp, N-margaroyl-Ala-Gln, N-margaroyl-Ala-Asn, N-margaroyl-Ala-Arg, N-margaroyl-Ala-Lys, N-margaroyl-Val-His, N-margaroyl-Val-Trp, N-margaroyl-Val-Gln, N-margaroyl-Val-Asn, N-margaroyl-Val-Arg, N-margaroyl-Val-Lys, N-margaroyl-Leu-His, N-margaroyl-Leu-Trp, N-margaroyl-Leu-Gln, N-margaroyl-Leu-Asn, N-margaroyl-Leu-Arg, N-margaroyl-Leu-Lys, N-margaroyl-Ile-His, N-margaroyl-Ile-Trp, N-margaroyl-Ile-Gln, N-margaroyl-Ile-Asn, N-margaroyl-Ile-Arg, N-margaroyl-Ile-Lys, N-stearoyl-Gly-His, N-stearoyl-Gly-Trp, N-stearoyl-Gly-Gln, N-stearoyl-Gly-Asn, N-stearoyl-Gly-Arg, N-stearoyl-Gly-Lys, N-stearoyl-Ala-His, N-stearoyl-Ala-Trp, N-stearoyl-Ala-Gln, N-stearoyl-Ala-Asn, N-stearoyl-Ala-Arg, N-stearoyl-Ala-Lys, N-stearoyl-Val-His, N-stearoyl-Val-Trp, N-stearoyl-Val-Gln, N-stearoyl-Val-Asn, N-stearoyl-Val-Arg, N-stearoyl-Val-Lys, N-stearoyl-Leu-His, N-stearoyl-Leu-Trp, N-stearoyl-Leu-Gln, N-stearoyl-Leu-Asn, N-stearoyl-Leu-Arg, N-stearoyl-Leu-Lys, N-stearoyl-Ile-His, N-stearoyl-Ile-Trp, N-stearoyl-Ile-Gln, N-stearoyl-Ile-Asn, N-stearoyl-Ile-Arg, N-stearoyl-Ile-Lys, N-elaidoyl-Gly-His, N-elaidoyl-Gly-Trp, N-elaidoyl-Gly-Gln, N-elaidoyl-Gly-Asn, N-elaidoyl-Gly-Arg, N-elaidoyl-Gly-Lys, N-elaidoyl-Ala-His, N-elaidoyl-Ala-Trp, N-elaidoyl-Ala-Gln, N-elaidoyl-Ala-Asn, N-elaidoyl-Ala-Arg, N-elaidoyl-Ala-Lys, N-elaidoyl-Val-His, N-elaidoyl-Val-Trp, N-elaidoyl-Val-Gln, N-elaidoyl-Val-Asn, N-elaidoyl-Val-Arg, N-elaidoyl-Val-Lys, N-elaidoyl-Leu-His, N-elaidoyl-Leu-Trp, N-elaidoyl-Leu-Gln, N-elaidoyl-Leu-Asn, N-elaidoyl-Leu-Arg, N-elaidoyl-Leu-Lys, N-elaidoyl-Ile-His, N-elaidoyl-Ile-Trp, N-elaidoyl-Ile-Gln, N-elaidoyl-Ile-Asn, N-elaidoyl-Ile-Arg, N-elaidoyl-Ile-Lys, N-arachidoyl-Gly-His, N-arachidoyl-Gly-Trp, N-arachidoyl-Gly-Gln, N-arachidoyl-Gly-Asn, N-arachidoyl-Gly-Arg, N-arachidoyl-Gly-Lys, N-arachidoyl-Ala-His, N-arachidoyl-Ala-Trp, N-arachidoyl-Ala-Gln, N-arachidoyl-Ala-Asn, N-arachidoyl-Ala-Arg, N-arachidoyl-Ala-Lys, N-arachidoyl-Val-His, N-arachidoyl-Val-Trp, N-arachidoyl-Val-Gln, N-arachidoyl-Val-Asn, N-arachidoyl-Val-Arg, N-arachidoyl-Val-Lys, N-arachidoyl-Leu-His, N-arachidoyl-Leu-Trp, N-arachidoyl-Leu-Gln, N-arachidoyl-Leu-Asn, N-arachidoyl-Leu-Arg, N-arachidoyl-Leu-Lys, N-arachidoyl-Ile-His, N-arachidoyl-Ile-Trp, N-arachidoyl-Ile-Gln, N-arachidoyl-Ile-Asn, N-arachidoyl-Ile-Arg, N-arachidoyl-Ile-Lys, N-behenoyl-Gly-His, N-behenoyl-Gly-Trp, N-behenoyl-Gly-Gln, N-behenoyl-Gly-Asn, N-behenoyl-Gly-Arg, N-behenoyl-Gly-Lys, N-behenoyl-Ala-His, N-behenoyl-Ala-Trp, N-behenoyl-Ala-Gln, N-behenoyl-Ala-Asn, N-behenoyl-Ala-Arg, N-behenoyl-Ala-Lys, N-behenoyl-Val-His, N-behenoyl-Val-Trp, N-behenoyl-Val-Gln, N-behenoyl-Val-Asn, N-behenoyl-Val-Arg, N-behenoyl-Val-Lys, N-behenoyl-Leu-His, N-behenoyl-Leu-Trp, N-behenoyl-Leu-Gln, N-behenoyl-Leu-Asn, N-behenoyl-Leu-Arg, N-behenoyl-Leu-Lys, N-behenoyl-Ile-His, N-behenoyl-Ile-Trp, N-behenoyl-Ile-Gln, N-behenoyl-Ile-Asn, N-behenoyl-Ile-Arg, and N-behenoyl-Ile-Lys.

Among the compounds, more preferable lipid peptide compounds are N-lauroyl-Gly-His, N-lauroyl-Gly-Trp, N-lauroyl-Gly-Gln, N-lauroyl-Gly-Asn, N-lauroyl-Gly-Lys, N-lauroyl-Ala-His, N-lauroyl-Ala-Trp, N-lauroyl-Ala-Gln, N-lauroyl-Ala-Asn, N-lauroyl-Ala-Lys, N-lauroyl-Val-His, N-lauroyl-Val-Trp, N-lauroyl-Val-Gln, N-lauroyl-Val-Asn, N-lauroyl-Val-Lys, N-myristoyl-Gly-His, N-myristoyl-Gly-Trp, N-myristoyl-Gly-Gln, N-myristoyl-Gly-Asn, N-myristoyl-Gly-Lys, N-myristoyl-Ala-His, N-myristoyl-Ala-Trp, N-myristoyl-Ala-Gln, N-myristoyl-Ala-Asn, N-myristoyl-Ala-Lys, N-myristoyl-Val-His, N-myristoyl-Val-Trp, N-myristoyl-Val-Gln, N-myristoyl-Val-Asn, N-myristoyl-Val-Lys, N-palmitoyl-Gly-His, N-palmitoyl-Gly-Trp, N-palmitoyl-Gly-Gln, N-palmitoyl-Gly-Asn, N-palmitoyl-Gly-Lys, N-palmitoyl-Ala-His, N-palmitoyl-Ala-Trp, N-palmitoyl-Ala-Gln, N-palmitoyl-Ala-Asn, N-palmitoyl-Ala-Lys, N-palmitoyl-Val-His, N-palmitoyl-Val-Trp, N-palmitoyl-Val-Gln, N-palmitoyl-Val-Asn, N-palmitoyl- Val-Lys, N-margaroyl-Gly-His, N-margaroyl-Gly-Trp, N-margaroyl-Gly-Gln, N-margaroyl-Gly-Asn, N-margaroyl-Gly-Lys, N-margaroyl-Ala-His, N-margaroyl-Ala-Trp, N-margaroyl-Ala-Gln, N-margaroyl-Ala-Asn, N-margaroyl-Ala-Lys, N-margaroyl-Val-His, N-margaroyl-Val-Trp, N-margaroyl-Val-Gln, N-margaroyl-Val-Asn, N-margaroyl-Val-Lys, N-margaroyl-Gly-His, N-margaroyl-Gly-Trp, N-margaroyl-Gly-Gln, N-margaroyl-Gly-Asn, N-margaroyl-Gly-Lys, N-margaroyl-Ala-His, N-margaroyl-Ala-Trp, N-margaroyl-Ala-Gln, N-margaroyl-Ala-Asn, N-margaroyl-Ala-Lys, N-margaroyl-Val-His, N-margaroyl-Val-Trp, N-margaroyl-Val-Gln, N-margaroyl-Val-Asn, N-margaroyl-Val-Lys, N-stearoyl-Gly-His, N-stearoyl-Gly-Trp, N-stearoyl-Gly-Gln, N-stearoyl-Gly-Asn, N-stearoyl-Gly-Lys, N-stearoyl-Ala-His, N-stearoyl-Ala-Trp, N-stearoyl-Ala-Gln, N-stearoyl-Ala-Asn, N-stearoyl-Ala-Lys, N-stearoyl-Val-His, N-stearoyl-Val-Trp, N-stearoyl-Val-Gln, N-stearoyl-Val-Asn, N-stearoyl-Val-Lys, N-elaidoyl-Gly-His, N-elaidoyl-Gly-Trp, N-elaidoyl-Gly-Gln, N-elaidoyl-Gly-Asn, N-elaidoyl-Gly-Lys, N-elaidoyl-Ala-His, N-elaidoyl-Ala-Trp, N-elaidoyl-Ala-Gln, N-elaidoyl-Ala-Asn, N-elaidoyl-Ala-Lys, N-elaidoyl-Val-His, N-elaidoyl-Val-Trp, N-elaidoyl-Val-Gln, N-elaidoyl-Val-Asn, N-elaidoyl-Val-Lys, N-arachidoyl-Gly-His, N-arachidoyl-Gly-Trp, N-arachidoyl-Gly-Gln, N-arachidoyl-Gly-Asn, N-arachidoyl-Gly-Lys, N-arachidoyl-Ala-His, N-arachidoyl-Ala-Trp, N-arachidoyl-Ala-Gln, N-arachidoyl-Ala-Asn, N-arachidoyl-Ala-Lys, N-arachidoyl-Val-His, N-arachidoyl-Val-Trp, N-arachidoyl-Val-Gln, N-arachidoyl-Val-Asn, N-arachidoyl-Val-Lys, N-behenoyl-Gly-His, N-behenoyl-Gly-Trp, N-behenoyl-Gly-Gln, N-behenoyl-Gly-Asn, N-behenoyl-Gly-Lys, N-behenoyl-Ala-His, N-behenoyl-Ala-Trp, N-behenoyl-Ala-Gln, N-behenoyl-Ala-Asn, N-behenoyl-Ala-Lys, N-behenoyl-Val-His, N-behenoyl-Val-Trp, N-behenoyl-Val-Gln, N-behenoyl-Val-Asn, and N-behenoyl-Val-Lys.

Most preferable compounds are N-lauroyl-Gly-His, N-lauroyl-Gly-Gln, N-lauroyl-Gly-Asn, N-lauroyl-Gly-Lys, N-myristoyl-Gly-His, N-myristoyl-Gly-Gln, N-myristoyl-Gly-Asn, N-myristoyl-Gly-Lys, N-palmitoyl-Gly-His, N-palmitoyl-Gly-Trp, N-palmitoyl-Gly-Gln, N-palmitoyl-Gly-Asn, N-palmitoyl-Gly-Lys, N-palmitoyl-Ala-His, N-palmitoyl-Ala-Trp, N-palmitoyl-Ala-Gln, N-palmitoyl-Ala-Asn, N-palmitoyl-Ala-Lys, N-palmitoyl-Val-His, N-palmitoyl-Val-Trp, N-palmitoyl-Val-Gln, N-palmitoyl-Val-Asn, N-palmitoyl-Val-Lys, N-margaroyl-Gly-His, N-margaroyl-Gly-Gln, N-margaroyl-Gly-Asn, N-margaroyl-Gly-Lys, N-margaroyl-Gly-His, N-margaroyl-Gly-Gln, N-margaroyl-Gly-Asn, N-margaroyl-Gly-Lys, N-stearoyl-Gly-His, N-stearoyl-Gly-Gln, N-stearoyl-Gly-Asn, N-stearoyl-Gly-Lys, N-elaidoyl-Gly-His, N-elaidoyl-Gly-Gln, N-elaidoyl-Gly-Asn, N-elaidoyl-Gly-Lys, N-arachidoyl-Gly-His, N-arachidoyl-Gly-Gln, N-arachidoyl-Gly-Asn, N-arachidoyl-Gly-Lys, N-behenoyl-Gly-His, N-behenoyl-Gly-Gln, N-behenoyl-Gly-Asn, and N-behenoyl-Gly-Lys.

[Fiber and Gel Formed from Gelator]

When the gelator of the present invention is put into water, an alcohol, an aqueous solution, an alcoholic solution, a hydrophilic organic solution, a higher alcohol, a fatty acid, higher fatty acid esters, a glyceride, a hydrophobic organic solution, or a miscible mixed solvent of them, a fibrous self-assembly is formed.

For example, when the gelator of the present invention is put into water, an alcohol, an aqueous solution, an alcoholic solution, or a hydrophilic organic solution, the peptide portion in Formula (1) forms intermolecular noncovalent bond through hydrogen bonds, while the lipid portion in Formula (1) is hydrophobically packed for self-assembly (also called self-organization), and thus a tubular secondary assembly, that is, a fiber is formed.

As reference, FIG. 1 shows an exemplified schematic diagram of self-assembly and gelation of the lipid peptides composing the gelator of the present invention (however, in the invention, not all of the lipid peptides form the self-assembly or the gel shown in FIG. 1).

The lipid peptide molecules (a) are assembled to place the lipid portions as the hydrophobic moieties at the center (b) and self-assembled to form a fiber (c).

When the gelator of the present invention is put into a higher alcohol, a fatty acid, a higher fatty acid ester, a glyceride, or a hydrophobic solution, the peptide portions in Formula (1) are conversely hydrophilically packed for self-assembly to form a self-assembly.

When the fiber is formed in an aqueous medium such as water, an alcohol, an aqueous solution, an alcoholic solution, or a hydrophilic organic solution, the fiber forms a three-dimensional network structure (for example, see FIG. 1(d)), and then noncovalent bonds are formed between the hydrophilic portion (peptide portion) on the fiber surface and the aqueous medium so that the fiber swells. Thus, gelation of the aqueous medium proceeds to form a hydrogel.

When the fiber is formed in the hydrophobic medium such as a higher alcohol, a fatty acid, a higher fatty acid ester, a glyceride, or a hydrophobic solution, the fiber forms a three-dimensional network structure, and then the hydrophobic portion (lipid portion) of the fiber surface and the hydrophobic medium are assembled through hydrophobic interactions. Thus, gelation of the hydrophobic medium proceeds to form a gel.

These gels can be formed in a sheet shape. Furthermore, when a solvent in the sheet-shaped gel is evaporated, a film can be prepared.

The aqueous medium is not specifically limited as far as the medium does not interfere with self-assembly, fiber formation, and gelation of the gelator. Specific usable examples of the preferred aqueous medium include water or an aqueous solution dissolving an inorganic salt or an organic salt in water (called an aqueous solution in the present specification), an alcohol or a mixed solution of water and an alcohol (called an alcoholic solution in the present specification), and a mixed solution of water and a hydrophilic organic solvent (called a hydrophilic organic solution in the present specification).

The alcohol is preferably a water-soluble alcohol freely dissolved in water, more preferably a $C_{1-6}$ alcohol, even more preferably methanol, ethanol, 2-propanol, i-butanol, or 1,3-butanediol, and specifically preferably ethanol or 2-propanol.

The hydrophilic organic solvent means an organic solvent other than alcohols and an organic solvent capable of being dissolved in water in any ratio. Usable examples of the hydrophilic organic solvent include acetone, dioxane, glycerin, polyethylene glycol, and propylene glycol.

A plurality of the acids or the salts may be added, and the acid and the salt may be mixed to be added. The number of acids or salts added is preferably 1 to 3. Two salts, or one or two acids and one or two salts are preferably added because the solution obtains buffering capacity.

The acid is an inorganic acid or an organic acid. Preferred examples of the inorganic acid include carbonic acid, sulfuric acid, and phosphoric acid. The inorganic acid is more preferably phosphoric acid and even more preferably phosphoric acid. Preferred examples of the organic acid include acetic acid, citric acid, succinic acid, and lactic acid. The organic acid is more preferably lactic acid.

Preferred examples of the inorganic salt include an inorganic lactate, an inorganic carbonate, an inorganic sulfate, an inorganic phosphate, and an inorganic hydrogen phosphate. The inorganic salt is more preferably potassium lactate, sodium lactate, calcium carbonate, sodium carbonate, potassium carbonate, sodium sulfate, potassium sulfate, magnesium sulfate, potassium phosphate, sodium phosphate, disodium hydrogen phosphate, or sodium dihydrogen phosphate, and even more preferably potassium lactate, sodium lactate, calcium carbonate, magnesium sulfate, disodium hydrogen phosphate, or sodium dihydrogen phosphate.

Preferred examples of the organic salt include a hydrochloride of organic amine or an acetate of organic amine. The organic salt is more preferably ethylenediamine hydrochloride, ethylenediaminetetraacetate, or trishydroxymethylaminomethane hydrochloride.

These inorganic salts and organic salts are commonly preferably dissolved in water before adding the gelator to be used as an aqueous solution, but may be added in any step in the process for forming a gel.

The hydrophobic medium is not specifically limited as far as the medium does not interfere with self-assembly, fiber formation, and gelation of the gelator. Specific usable examples of the preferred hydrophobic medium include the higher alcohols, the fatty acids, the higher fatty acid esters, the glycerides, and a solution of other hydrophobic organic solvents (called a hydrophobic solution in the present specification).

Examples of the higher alcohol include stearyl alcohol and oleyl alcohol, and examples of the fatty acid include stearic acid.

Examples of the higher fatty acid ester include cetyl octanoate, isopropyl myristate, and isopropyl palmitate.

Examples of the glyceride include trioctanoin, glyceryl tri(caprylate/caprate), and glyceryl stearate.

Examples of the hydrophobic organic solvent include vegetable oils such as olive oil, coconut oil, castor oil, jojoba oil, and sunflower seed oil and hydrocarbons such as mineral oils, hydrogenated isobutene, and liquid paraffin.

Among the aqueous mediums and the hydrophobic mediums, specifically preferred mediums are water, 2-propanol, i-butanol, glycerin, polyethylene glycol, an ethanol aqueous solution, a 2-propanol solution, an i-butanol solution, a propylene glycol solution, a glycerin solution, a polyethylene glycol solution, a 1,3-butanediol solution, a stearyl alcoholic solution, an oleyl alcohol solution, and a liquid paraffin solution.

As the gelator used for forming a fiber or a gel, the gelator including the lipid peptide of Formula (1) of the present invention may be used singly or as a mixture of two or more of the gelators. One or two gelators are preferably used, and more preferably one gelator is used. When two gelators are used, the obtained gel is expected to have characteristics different from those from one agent.

A gelator other than the gelator including the lipid peptide of Formula (1) of the present invention, for example, a gelator including a lipid peptide of Formula (2) below or its pharmaceutically usable salt may be used as a mixture.

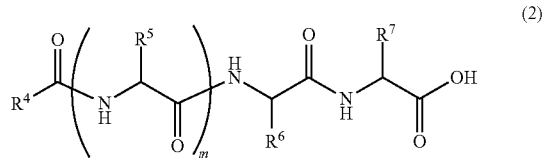

(2)

In Formula (2), $R^4$ is a $C_{9-23}$ aliphatic group, each of $R^5$, $R^6$, and $R^7$ is hydrogen, a $C_{1-4}$ alkyl chain optionally having a $C_{1-2}$ branched chain, or —$(CH_2)_n$—X and at least one or more of $R^5$, $R^6$, and $R^7$ is —$(CH_2)_n$—X, n is a number from 1 to 4, X is an amino group, a guanidino group, a —$CONH_2$ group, or a 5-membered ring, a 6-membered ring, or a fused heterocycle including a 5-membered ring and a 6-membered ring optionally having 1 to 3 nitrogen atoms, and m is a number from 1 to 4.

When the gelator of the present invention is used in combination with a surfactant at the time of putting into a hydrophilic medium or a hydrophobic medium, fiber formation and gel formation can be accelerated. Examples of the surfactant include an anionic surfactant, a nonionic surfactant, and a cationic surfactant.

The present invention is directed a gel that is formed by adhesion or inclusion of a low-molecular weight compound into the fiber.

The gelator (lipid peptide) forming the fiber and the gel of the present invention has the hydrophilic moiety and the hydrophobic moiety in the molecule as described above. Thus, for example, when the fiber simultaneously adheres to or includes a hydrophobic low-molecular weight compound such as vitamin E and a hydrophilic low-molecular weight compound such as a vitamin C derivative, the low-molecular weight compounds can be dissolved in various solvents.

Furthermore, a compound having poor water solubility such as an antiseptic can be solubilized.

Specific examples of the low-molecular weight compound capable of adhesion or inclusion into the fiber include a hydrophobic compound, a hydrophilic compound, a poorly soluble compound, an enzyme, and pyrene.

Examples of the hydrophobic compound include vitamin E (tocopherol), pyrene, azelaic acid derivatives, retinol (vitamin A alcohol), retinoic acid, hydroxycinnamic acid, caffeine, hinokitiol, carotenoids, astaxanthin, steroids, indomethacin, and ketoprofen.

Examples of the hydrophilic compound include vitamin C (ascorbic acid), vitamin B2 (riboflavin), kojic acid, glucosamine, azelaic acid, pyridoxine (vitamin B6), pantothenic acid (vitamin B5), arbutin, and chitosan.

Examples of the poorly soluble compound include phenoxyethanol and methylparaben.

Examples of the enzyme include cytochrome c.

When the fiber includes, as the low-molecular weight compound, for example, ascorbic acid and its derivatives, kojic acid and its derivatives, glucosamine and its derivatives, azelain and its derivatives, retinol acid and its derivatives, pyridoxine and its derivatives, pantothenic acid and its derivatives, arbutin and its derivatives, tocopherol and its derivatives, hydroxycinnamic acid and its derivatives, chitosan, chitosan degradation products, caffeine derivatives, hinokitiol, carotenoids, and astaxanthin, a gel capable of providing a whitening effect can be formed.

When a gel formed from the fiber is in contact with a liquid or a living body, the gel can gradually release a contained low-molecular weight compound, that is, can have so-called sustained-releasing properties. Examples of the low-molecular weight compound include medical drugs, agrochemicals, and functional low-molecular weight compounds.

Detailed mechanisms during formation of the gel of the present invention are unknown but a charge state of the lipid peptide molecule is supposed to be involved.

The lipid peptide of the present invention is a zwitterionic compound having a carboxy group at the C-terminal and an amino group derived from a —$(CH_2)_n$—X group that is a side chain of the peptide portion. Its ionic state is supposed to be in equilibrium under four states, that is, the state in which only the carboxy group is negatively charged, the state in which only the amino group is positively charged, the state in which both of the groups are charged to be zwitterionic, and the state in which neither of the groups is charged.

Considering the acid dissociation constant of an amino acid residue, it is supposed that, in the lipid peptide molecule, the terminal amino group derived from the —$(CH_2)_n$—X group of the peptide portion is positively charged to become a positive ion in an acidic region, the terminal carboxy group at the C-terminal of the peptide portion is negatively charged to become a negative ion in a basic region, and the molecule mainly becomes a zwitterion in a neutral region.

When the molecule is ionized, the affinity of the peptide portion with water increases. Then, the molecules are self-assembled so that the long chain part as the hydrophobic moiety will not be in contact with water, and a nanofiber is formed. At that time, when the zwitterions are predominantly present, positive ions and negative ions are ionically bonded between nanofibers to form a cross-linked network structure. When the network structure is formed, a larger amount of water can be incorporated, and thus excellent gel forming ability is supposed to be provided.

Furthermore, such fiber obtained by the self-assembly of the low-molecular weight compounds does not fall off from the network structure formed from self-assembled fibers, unlike the fiber obtained by the self-assembly of natural polymer compounds. Moreover, the gelator does not fall off one molecule by one molecule from the self-assembly, and thus a gel is not disintegrated.

When the gelator of the present invention is added especially into a hydrophobic organic solution, in some cases, into a hydrophilic solvent and a solvent such as a higher alcohol, a fatty acid, and a fatty acid ester, it is also supposed that the peptide portions are assembled at the center, the lipid portions are assembled on the surface part to form a fiber, and then a three dimensional network structure is similarly formed to form a gel.

The gelator of the present invention is a lipid peptide composed of a fatty acid having an appropriate number of carbon atoms and a dipeptide, and thus has an adequate balance between a size of the hydrophobic moiety and a size of the hydrophilic moiety. Consequently, it is supposed that the assembling patterns can be changed both in an aqueous solution and an organic solution, and thus a gel can be formed in both an aqueous solution and an organic solvent.

As described above, the gelator of the present invention can form a stable gel in a neutral region. Furthermore, the gelator of the present invention is a low-molecular weight compound, and thus the gelator and the formed fiber and gel are degradable in an environment and a living body. Therefore, a gelator and a gel having high biocompatibility can be obtained.

On this account, the lipid peptide of the present invention and the obtained gel therefrom can be used as materials in various fields such as cell culture carriers, storage materials for biomolecules such as cells and proteins, base materials for external preparations, materials for medical use, biochemical materials, cosmetic materials, food materials, contact lenses, disposable diapers, artificial actuators, dryland farming materials. Furthermore, they can widely be used as bioreactor carriers for enzymes and the like for researches, medical cares, analyses, and various industries.

The gel of the present invention is a gel composed of a low-molecular weight compound (lipid peptide). Thus, depending on a design of the compound, various functions can be readily added without polymer chain modification or copolymerization reaction, for example, a gel that performs sol-gel transformation by external stimulus response can be formed.

The present invention is directed to a novel lipid peptide. The novel lipid peptide is a lipid peptide of Formula (1b):

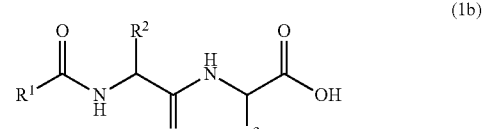

(where $R^1$ is a $C_{1-22}$ aliphatic group, $R^2$ is a hydrogen atom, and $R^3$ is a 3-indole methyl group or an imidazole methyl group) and its pharmaceutically usable salt.

Alternatively, it is a lipid peptide of Formula (1c):

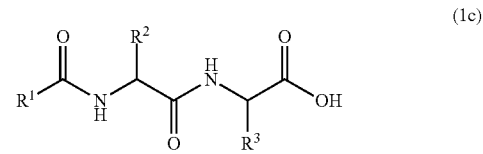

(where $R^1$ is a $C_{14-22}$ aliphatic group, $R^2$ is a hydrogen atom, a methyl group, an isopropyl group, an isobutyl group, or a 2-butyl group, and $R^3$ is a 4-amino-n-butyl group, a carbamoylethyl group, a carbamoylmethyl group, an imidazole methyl group, or a 3-indole methyl group) and its pharmaceutically usable salt.

In Formula (1c), it is preferable that $R^2$ be a methyl group, an isopropyl group, an isobutyl group, or a 2-butyl group, and $R^3$ be a 4-amino-n-butyl group, a carbamoylethyl group, or a carbamoylmethyl group.

Alternatively, in Formula (1c), it is preferable that $R^2$ be a methyl group, an isopropyl group, an isobutyl group, or a 2-butyl group, and $R^3$ be an imidazole methyl group or a 3-indole methyl group.

Furthermore, in Formula (1c), it is preferable that $R^2$ be a hydrogen atom, and $R^3$ be a 4-amino-n-butyl group, a carbamoylethyl group, or a carbamoylmethyl group.

The present invention is also directed to a gelator characterized by including a lipid peptide of Formula (3) below or its pharmaceutically usable salt, and a lipid peptide of Formula (3) or its pharmaceutically usable salt.

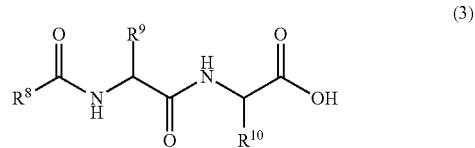

In Formula (3), $R^8$ is a $C_{9-23}$ aliphatic group, $R^9$ is a —$(CH_2)_n$—X group, $R^{10}$ is a hydrogen atom or a $C_{1-4}$ alkyl group optionally having a $C_{1-2}$ branched chain, n is a number from 1 to 4, and X is an amino group, a guanidino group, a —$CONH_2$ group, or a 5-membered ring, a 6-membered ring, or a fused heterocycle including a 5-membered ring and a 6-membered ring optionally having 1 to 3 nitrogen atoms.

EXAMPLES

Hereinafter, the present invention will be described in further detail with reference to examples, but the present invention is not limited to these examples.

[Abbreviations Used in Examples]

Abbreviations used in the below examples mean the following compounds.

Gly: glycine
His: histidine
Val: valine
Ala: alanine
Gln: glutamine
Lys: lysine
Trp: tryptophan
HBTU: 2-(1H-benzotriazol-1-yl)-1,1,3,3-tetramethyluronium-hexafluorophosphate (Watanabe Chemical Industries, Ltd.)
HOBt: 1-hydroxy-benzotriazole (Peptide Institute, Inc.)
DMF: N,N-dimethylformamide
WSCD: 1-ethyl-3-(3-dimethylaminopropyl)carbodiimide
TFA: trifluoroacetic acid (Watanabe Chemical Industries, Ltd.)
TIS: triisopropylsilane (Watanabe Chemical Industries, Ltd.)
NMP: N-methyl-2-pyrrolidone
DIPEA: N,N-diisopropylethylamine (Tokyo Chemical Industry Co., Ltd.)
DMSO: dimethylsulfoxide

[Lipid Peptide]

A lipid peptide was synthesized according to the procedure of Fmoc solid phase peptide synthesis shown below. An amino acid-Barlos Resin was mainly used as the resin. The synthesis was performed under a synthesis scale of 0.3 mmol.

Example 1

Phase Synthesis of
N-Palmitoyl-Gly-His.Trifluoroacetate (TFA Salt)

To a peptide synthesizer, a reaction container including 163 mg (0.125 mmol) of H-His(Trt)-Trt(2-Cl) resin (0.77 mmol of His per gram of the resin was added) (Watanabe Chemical Industries, Ltd.) was installed, and 149 mg (4 eq) of Fmoc-Gly-OH (Watanabe Chemical Industries, Ltd.) was condensed by Fmoc method to give a H-Gly-His(Trt)-Trt(2-Cl) resin.

The obtained wet peptide resin was transferred to a manual reactor, and 160 mg (5 eq) of palmitic acid (Aldrich), 85 mg (5 eq) of HOBt, 235 mg (5 eq) of HBTU, 1 ml of DMF, and 2 ml of NMP were added. The whole was stirred and then 0.22 ml of DIPEA was added. After 1 hour stirring, a small amount of the resin was sampled to confirm the reaction completion. The reacted solution was filtered. Then, the resin was successively washed with NMP and methanol and then dried under reduced pressure to give 187 mg of N-palmitoyl-Gly-His(Trt)-Trt(2-Cl) resin.

A total amount of the dried resin was treated with 1.8 ml of TFA-TIS-water (95:2.5:2.5), and 37 mg of the obtained crude peptide was purified with a preparative HPLC system using an ODS column. An eluted fraction having a desired purity was collected, and acetonitrile was removed by evaporation. Then, the residue was further lyophilized to give 32 mg of N-palmitoyl-Gly-His.TFA salt.

$^1$H-NMR (300 MHz, DMSO-$d_6$, δ ppm): 8.96 (1H, s), 8.21 (1H, d, J=8.4 Hz), 8.04 (1H, t, J=6.3 Hz), 7.36 (1H, s), 4.57-4.50 (1H, m), 3.65 (2H, d, J=6.3 Hz), 3.14 (1H, m), 2.99 (1H, m), 2.10 (2H, t, J=7.5 Hz), 1.47 (2H, m), 1.23 (24H, s), 0.85 (3H, t, J=6.6 Hz).

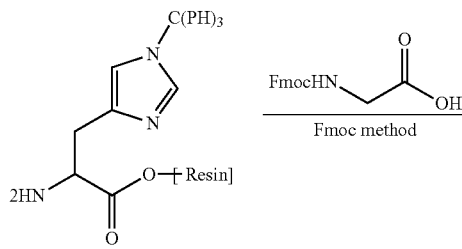

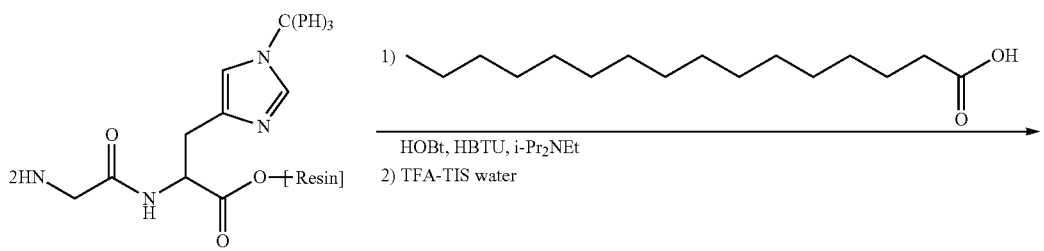

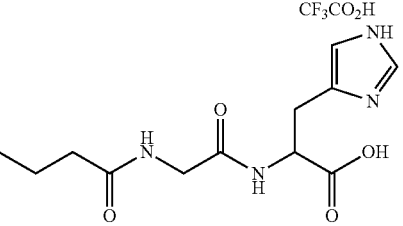

MS (EI) m/z: 451.4 (M$^+$+1, bp).
Conditions for HPLC Purification:
Column: YMC-Pack ODS-A (250×20 mm I.D.)
Flow rate: 10 mL/min
Elution: MeCN/0.1% TFA aq.=45/55-(80 minutes, liner gradient)-65/35
Detection wavelength: 220 nm
Temperature: room temperature Example 2

Liquid Phase Synthesis of N-Palmitoyl-Gly-His.TFA Salt

Synthesis of N-Palmitoyl-Gly-OtBu

Gly-tBu.HCl (8.82 g, 52.6 mmol) and palmitoyl chloride (15.2 ml, 50.1 mmol) were dissolved in 200 ml of chloroform. Triethylamine (14.6 ml, 105 mmol) was added dropwise to the solution with stirring while cooling with ice over 10 minutes, and then the reaction solution was allowed to gradually reach room temperature and stirred for 15 hours. Water was added, and then the water was separated. Then, the organic phase was washed with a saturated saline solution and dried over magnesium sulfate. After concentration under reduced pressure, the residue was washed with hexane and filtered to give 17.4 g (94%) of a target compound as a colorless solid.
$^1$H-NMR (300 MHz, DMSO-d$_6$, δ ppm): 8.09 (1H, t, J=6.3 Hz), 3.67 (2H, d, J=6.3 Hz), 2.09 (2H, t, J=7.8 Hz), 1.48 (2H, m), 1.39 (9H, s), 1.23 (24H, brs), 0.85 (3H, t, J=6.9 Hz).
MS (EI) m/z: 314.3 (M$^+$-Boc-1, bp).

Synthesis of N-Palmitoyl-Gly

To N-palmitoyl-Gly-OtBu (17.4 g, 47.1 mmol), 4M HCl/AcOEt (118 ml, 0.471 mmol) was added and the whole was stirred at room temperature for 1 hour. After concentration under reduced pressure, the residue was washed with hexane to give 11.4 g (77%) of a target compound as colorless powder.
$^1$H-NMR (300 MHz, DMSO-d$_6$, δ ppm): 12.43 (1H, brs), 8.07 (1H, t, J=5.7 Hz), 3.70 (2H, d, J=5.7 Hz), 2.09 (2H, t, J=7.8 Hz), 1.47 (2H, m), 1.23 (24H, brs), 0.85 (3H, t, J=6.9 Hz).

Synthesis of N-Palmitoyl-Gly-His(Trt)-OtBu

His(Trt)-OtBu (15.0 g, 33.1 mmol) and HOBt.H$_2$O (5.13 g, 33.5 mmol) were added to N-palmitoyl-Gly (10.0 g, 31.9 mmol), and the whole was stirred while cooled with ice. Then, WSCD hydrochloride (6.42 g, 33.5 mmol) was added, and the whole was stirred while cooled with ice for 30 minutes and further stirred at room temperature for 18 hours. Water (500 ml) and ethyl acetate (400 ml) were added, and then, the aqueous phase was extracted with ethyl acetate (200 ml). The combined organic phase was successively washed with a saturated aqueous sodium hydrogen carbonate solution, a saturated saline solution, 10% citric acid aqueous solution, and a saturated saline solution, and dried over magnesium sulfate. The organic phase was concentrated under reduced pressure to give 28.1 g (118%) of a target compound as a pale yellow oily substance.
$^1$H-NMR (300 MHz, DMSO-d$_6$, δ ppm): 7.77 (1H, d, J=7.8 Hz), 7.35-7.29 (10H, m), 7.13-7.07 (6H, m), 6.64-6.58 (2H, m), 4.67 (1H, m), 3.98 (2H, m), 2.98 (2H, m), 2.22 (2H, m), 1.61 (2H, m), 1.34 (9H, s), 1.25 (24H, brs), 0.87 (3H, t, J=6.6 Hz).

Synthesis of N-Palmitoyl-Gly-His.TFA Salt

A mixture of TFA (206 ml), triisopropylsilane (10.8 ml), and H$_2$O (10.8 ml) was added to N-palmitoyl-Gly-His(Trt)-OtBu (23.0 g, 30.8 mmol) while cooling with ice and the whole was stirred at room temperature for 1 hour. After concentration under reduced pressure, the residue was washed with diisopropyl ether and then diethyl ether, and then collected by filtration with a membrane-filter. The residue was reprecipitated with TFA (35 ml) and diethyl ether (800 ml), and the precipitate was dried under reduced pressure to give 16.2 g (93%) of a target compound.

Example 3

Synthesis of N-Palmitoyl-Gly-His.TFA Salt without Protection

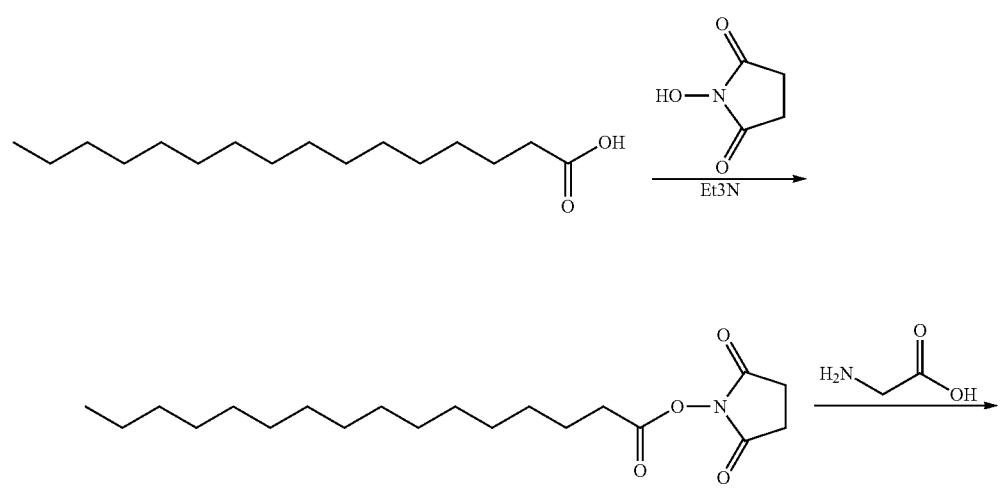

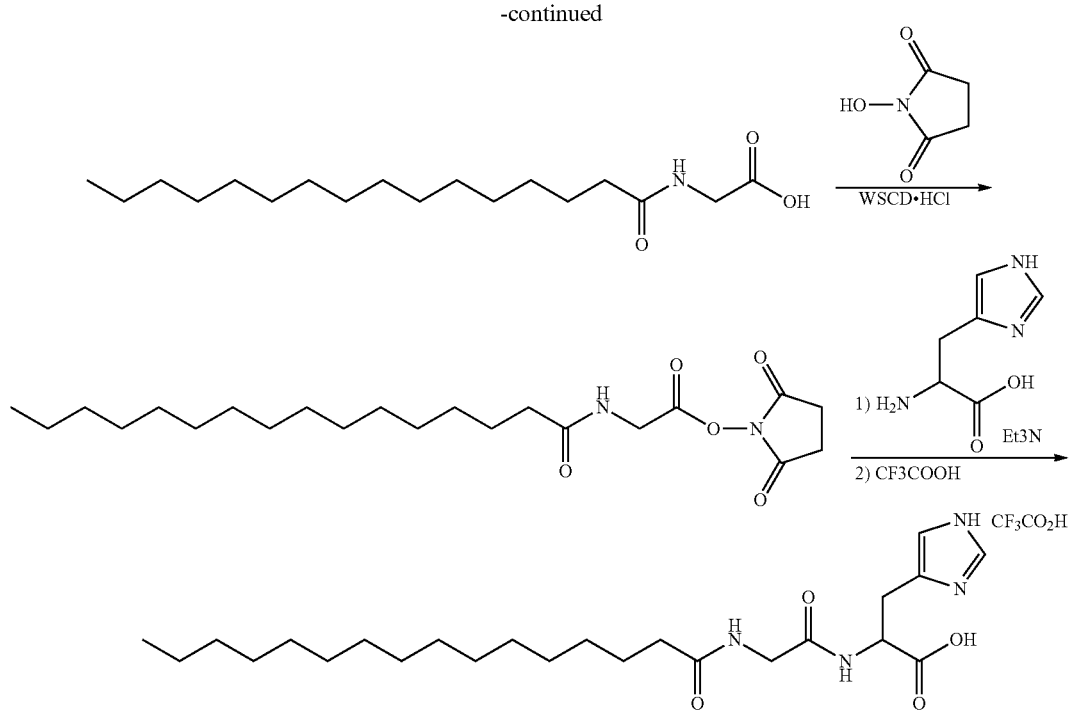

Synthesis of N-Palmitoyloxy-Succinimide

N-hydroxysuccinimide (69.8 g, 0.598 mol) was added drop by drop to 1 L of chloroform solution of palmitoyl chloride (165 ml, 0.544 mol) with stirring while cooling with ice, and then triethylamine (83.1 ml, 0.598 mol) was added dropwise over 30 minutes. Then, the whole was stirred while cooled with ice for 30 minutes, allowed to gradually reach room temperature, and stirred for 7 hours. The reaction mixture was washed with water (500 ml×3), then dried over magnesium sulfate, and concentrated under reduced pressure to give 260.3 g (quant) of a colorless solid.

$^1$H-NMR (300 MHz, DMSO-d$_6$, δ ppm): 2.80 (4H, s), 2.65 (2H, t, J=7.2 Hz), 1.61 (2H, quintet, J=7.2 Hz), 1.24 (24H, s), 0.85 (3H, t, J=6.3 Hz).

Synthesis of N-Palmitoyl-Gly

A total amount (260.3 g) of N-palmitoyloxy-succinimide synthesized above was suspended in 750 ml of DMF. To the suspension, a solution of Gly (56.3 g, 0.750 mol) and triethylamine (83.2 ml, 0.598 mol) in 250 ml of water was added dropwise with stirring while cooling with ice. The whole was stirred for 30 minutes while cooled with ice, then allowed to gradually reach room temperature, and stirred for 15 hours. An aqueous solution with pH 3 that was prepared by dissolving 100 ml of 6N hydrochloric acid in 1 L of water was stirred while cooled with ice. The reaction solution containing N-palmitoyloxy-succinimide was added dropwise to the aqueous solution. The precipitated solid was collected by filtration. The precipitated solid was washed with 2 L of water and then 1 L of hexane, and recovered to give 114 g (67%) of a target compound.

$^1$H-NMR (300 MHz, DMSO-d$_6$, δ ppm): 8.10 (1H, t, J=6 Hz), 3.71 (2H, d, J=6 Hz), 2.10 (2H, t, J=7.2 Hz), 1.48 (2H, m), 1.23 (24H, s), 0.85 (3H, t, J=6.3 Hz).

Synthesis of N-Palmitoyloxy-Glycyloxysuccinimide

In 620 ml of DMF, 114 g (0.364 mol) of N-palmitoyl-Gly synthesized above and N-hydroxysuccinimide (44.0 g, 0.382 mol) were suspended, and the whole was stirred while cooled with ice. WSCD hydrochloride (73.2 g, 0.382 mol) was added into the suspension. The whole was stirred while cooled with ice for 30 minutes and further stirred at room temperature for 20 hours. To the reaction mixture, 1.5 L of ice water was added. An insoluble was collected by filtration, washed with 5 L of water, and then washed with 1.5 L of ether. Then, the obtained solid was dried under reduced pressure to give 198 g of a colorless solid quantitatively.

$^1$H-NMR (300 MHz, DMSO-d$_6$, δ ppm): 8.46 (1H, t, J=5.7 Hz), 4.22 (2H, d, J=5.7 Hz), 2.89 (4H, s), 2.13 (2H, t, J=7.2 Hz), 1.49 (2H, m), 1.23 (24H, s), 0.85 (3H, t, J=6.3 Hz).

Synthesis of N-Palmitoyl-Gly-His.TFA Salt

A total amount of 198 g of N-palmitoyloxy-glycyloxysuccinimide synthesized above was suspended in DMF, and a suspension of 113 g (0.728 mol) of L-histidine and 55.6 ml (0.400 mol) of triethylamine in 350 ml of water was added with stirring while cooling with ice. Then, the whole was stirred while cooled with ice for 30 minutes, then allowed to reach room temperature, and further stirred for 17 hours. A precipitated solid was collected by filtration without treatment to give a solid. The solid was added into a solution mixed with 120 ml of trifluoroacetic acid and 1.5 L of ice water. The whole was stirred, and then an insoluble was collected by filtration. The obtained solid was charged into a jug, washed with 2 L of water three times, and then dried under reduced pressure. The obtained dried solid was dissolved in 400 ml of trifluoroacetic acid, and a small amount of insoluble was filtered off with a membrane-filter. The filtrate was concentrated under reduced pressure to about half the volume. Then, a solid was washed with diethyl ether and dried under reduced pressure. The solid was washed with water several times, and the obtained solid was dried under reduced pressure to give 112 g (54%) of a colorless solid.

Example 4

Synthesis of Free N-Palmitoyl-Gly-His

To 2.0 g (4.86 mmol) of N-palmitoyloxy-glycyloxysuccinimide as the synthetic intermediate in Example 3, 175 mL of DMF was added, and the whole was cooled in an ice bath. Then, 45 mL of water, 0.74 mL (5.46 mmol, 1.1 eq) of triethylamine, and 1.50 g (9.72 mmol, 2.0 eq) of H-L-His-OH were added, and the whole was reacted for 30 minutes. The reaction mixture was left to reach room temperature, and then reacted at room temperature for 23.5 hours.

After the completion of the reaction, the reaction solution (gel) was centrifuged (4° C., 10,000 rpm, for 15 minutes) and lyophilized (7 hours×2). The gel product with the supernatant liquid removed was dissolved in 350 mL of methanol. Insolubles were filtered off, and the filtrate was concentrated under reduced pressure to make a liquid (A).

Separately, the supernatant liquid (DMF/aqueous layer) after the centrifugation was cooled in a refrigerator for 15 hours, and centrifuged (4° C., 10,000 rpm, for 25 minutes). Then, the supernatant liquid was removed and the residue was lyophilized (7 hours×3). Then, the product was dissolved in 250 mL of methanol, and insolubles were filtered off to make a liquid (B).

The liquid (B) was added to the liquid (A), and the mixture was concentrated under reduced pressure. The residue was washed with 150 mL of chloroform and 150 mL of water to give 698.3 mg (32%) of a white solid.

$^1$H-NMR (300 MHz, DMSO-$d_6$, δ ppm): 8.12 (1H, d, J=7.8 Hz), 8.06 (1H, t, J=5.7 Hz), 7.56 (1H, s), 6.81 (1H, s), 4.38 (1H, q, J=7.8 Hz), 3.69 (2H, dd, J=5.7 Hz and J=10.2 Hz), 2.89 (2H, m), 2.20 (2H, t, J=6.9 Hz), 1.48 (2H, m), 1.23 (24H, s), 0.85 (3H, t, J=7.2 Hz).

MS (EI) m/z: 451.43 ($M^+$+1, bp).

Example 5

Neutralization of N-Palmitoyl-Gly-His.TFA Salt

Into a sample bottle, 500 mg of N-palmitoyl-Gly-His trifluoroacetate was weighed and placed. Into the bottle, 10 ml of milli-Q water was added, then 17.7 ml of 0.05M sodium hydroxide aqueous solution was added, and the whole was mixed. The bottle was placed in a water bath at 90° C. and the contents were completely dissolved while gently shaking. After allowing to cool, the mixture was lyophilized. The obtained solid was washed with water several times, and then dried under reduced pressure to give 399 g of a neutralized product quantitatively.

Example 6

Synthesis of N-Lauroyl-Gly-His.TFA Salt

In a similar procedure to that in Example 1, that is, the H-His(Trt)-Trt(2-Cl) resin was installed; Fmoc-Gly-OH was condensed by the Fmoc method; finally, lauric acid (Aldrich) was reacted; and the product was treated with TFA-TIS-water to give a target compound in a yield of 82%.

$^1$H-NMR (300 MHz, DMSO-$d_6$, δ ppm): 8.59 (1H, s), 8.19 (1H, d, J=7.4 Hz), 8.05 (1H, t, J=5.7 Hz), 7.22 (1H, s), 4.50 (1H, m), 3.65 (2H, d, J=5.7 Hz), 3.02 (2H, m), 2.11 (2H, t, J=8.1 Hz), 1.47 (2H, m), 1.23 (16H, brs), 0.85 (3H, t, J=6.9 Hz).

MS (EI) m/z: 395.4 ($M^+$+1, bp), 214.9.

Example 7

Synthesis of N-Behenoyl-Gly-His.TFA Salt

In a similar procedure to that in Example 1, that is, the H-His(Trt)-Trt(2-Cl) resin was installed; Fmoc-Gly-OH was condensed by the Fmoc method; finally, behenic acid (Aldrich) was reacted; and the product was treated with TFA-TIS-water to give a target compound in a yield of 82%.

$^1$H-NMR (300 MHz, DMSO-$d_6$, δ ppm): 8.45 (1H, s), 8.18 (1H, d, J=8.4 Hz), 8.05 (1H, t, J=5.7 Hz), 7.16 (1H, s), 4.48 (1H, m), 3.65 (2H, d, J=5.7 Hz), 3.00 (2H, m), 2.10 (2H, t, J=7.5 Hz), 1.47 (2H, m), 1.23 (36H, brs), 0.85 (3H, t, J=7.2 Hz).

MS (EI) m/z: 535.6 ($M^+$+1, bp), 363.3, 270.1.

Example 8

Synthesis of N-Myristoyl-Gly-His.TFA Salt

In a similar procedure to that in Example 1, that is, the H-His(Trt)-Trt(2-Cl) resin was installed; Fmoc-Gly-OH was condensed by the Fmoc method; finally, myristic acid (Aldrich) was reacted; and the product was treated with TFA-TIS-water to give a target compound in a yield of 89%.

$^1$H-NMR (300 MHz, DMSO-$d_6$, δ ppm): 8.93 (1H, s), 8.22 (1H, d, J=8.4 Hz), 8.05 (1H, t, J=5.7 Hz), 7.35 (1H, s), 4.50 (1H, m), 3.65 (2H, d, J=5.7 Hz), 3.06 (2H, m), 2.10 (2H, t, J=7.5 Hz), 1.46 (2H, m), 1.23 (20H, brs), 0.85 (3H, t, J=6.6 Hz).

MS (EI) m/z: 423.4 ($M^+$+1, bp).

Example 9

Synthesis of N-Palmitoyl-Gly-Lys.TFA Salt

In a similar procedure to that in Example 1, but an H-Lys(Boc) Resin was installed; Fmoc-Gly-OH was condensed by the Fmoc method; finally, palmitic acid (Aldrich) was reacted; and the product was treated with TFA-TIS-water to give a target compound.

$^1$H-NMR (300 MHz, DMSO-$d_6$, δ ppm): 8.05-7.98 (2H, m), 7.66 (2H, brs), 4.18 (1H, m), 3.70 (2H, m), 2.76 (2H, m), 2.10 (2H, t, J=7.2 Hz), 1.73-1.47 (6H, m), 1.37-1.23 (26H, brs), 0.85 (3H, t, J=6.6 Hz).

MS (EI) m/z: 423.4 ($M^+$+1, bp).

Example 10

Synthesis of N-Palmitoyl-Ala-His.TFA salt

In a similar procedure to that in Example 1, that is, the H-His(Trt)-Trt(2-Cl) resin was installed; Fmoc-Ala-OH was condensed by the Fmoc method; finally, palmitic acid (Aldrich) was reacted; and the product was treated with TFA-TIS-water to give a target compound.

$^1$H-NMR (300 MHz, DMSO-$d_6$, δ ppm): 8.49 (1H, s), 8.20 (1H, d, J=8.1 Hz), 7.97 (1H, d, J=7.2 Hz), 7.20 (1H, s), 4.47 (1H, m), 4.23 (1H, m), 3.07 (2H, m), 2.07 (2H, t, J=6.9 Hz), 1.45 (2H, m), 1.23 (24H, brs), 1.16 (3H, d, J=6.9 Hz), 0.85 (3H, t, J=6.6 Hz).

MS (EI) m/z: 442.4 ($M^+$+1, bp), 297.2.

Example 11

Synthesis of N-Palmitoyl-Val-His.TFA Salt

In a similar procedure to that in Example 1, that is, the H-His(Trt)-Trt(2-Cl) resin was installed; Fmoc-Val-OH was condensed by the Fmoc method; finally, palmitic acid (Aldrich) was reacted; and the product was treated with TFA-TIS-water to give a target compound.

$^1$H-NMR (300 MHz, DMSO-$d_6$, δ ppm): 8.53 (1H, s), 8.31 (1H, d, J=7.5 Hz), 7.82 (1H, d, J=8.7 Hz), 7.20 (1H, s), 4.49 (1H, m), 4.09 (1H, t, J=7.5 Hz), 3.00 (2H, m), 2.22-1.89 (3H, m), 1.47 (2H, m), 1.23 (24H, brs), 0.83 (9H, m).

MS (EI) m/z: 493.4 ($M^+$+1, bp).

Example 12

Synthesis of N-Palmitoyl-Gly-Trp.TFA salt

In a similar procedure to that in Example 1, but a Trp(Boc) Alko resin (Watanabe Chemical Industries, Ltd.) was installed; Fmoc-Gly-OH was condensed by the Fmoc method; finally, palmitic acid (Aldrich) was reacted; and the product was treated with TFA-TIS-water to give a target compound.

$^1$H-NMR (300 MHz, DMSO-$d_6$, δ ppm): 10.83 (1H, s), 7.99-7.91 (2H, m), 7.50 (1H, d, J=7.8 Hz), 7.31 (1H, d, J=8.4 Hz), 7.21-6.94 (3H, m), 4.47 (1H, m), 3.67 (2H, m), 3.17 (1H, m), 3.02 (1H, m), 2.07 (2H, t, J=7.2 Hz), 1.45 (23H, m), 1.23 (24H, brs), 0.85 (3H, t, J=6.6 Hz).

MS (EI) m/z: 500.4 ($M^+$+1, bp), 205.1.

Example 13

Synthesis of N-Palmitoyl-Gly-Gln.TFA Salt

In a similar procedure to that in Example 1, but a Gln(Trt)-Alko (Watanabe Chemical Industries, Ltd.) was installed; Fmoc-Gly-OH was condensed by the Fmoc method; finally, palmitic acid (Aldrich) was reacted; and the product was treated with TFA-TIS-water to give a target compound.

$^1$H-NMR (300 MHz, DMSO-$d_6$, δ ppm): 8.07 (1H, d, J=7.5 Hz), 7.95 (1H, m), 4.16 (1H, m), 3.70 (2H, m), 2.10-2.08 (4H, m), 1.92 (1H, m), 1.75 (1H, m), 1.47 (2H, m), 1.23 (24H, brs), 0.85 (3H, t, J=6.6 Hz).

MS (EI) m/z: 442.3 ($M^+$+1, bp), 130.1.

Example 14

Synthesis of N-Palmitoyl-His-Gly.TFA Salt

In a similar procedure to that in Example 1, but a glycine Alko Resin was installed; Fmoc-His-OH was condensed by the Fmoc method; finally, palmitic acid (Aldrich) was reacted; and the product was treated with TFA-TIS-water to give a target compound.

$^1$H-NMR (300 MHz, DMSO-$d_6$, δ ppm): 8.70 (1H, s, C-2 His), 8.22 (1H, t, J=6 Hz, NH Gly), 8.07 (1H, d, J=8.7 Hz, NH His), 7.22 (1H, s, C-5 His), 4.62 (1H, m, α-CH His), 3.84-3.67 (2H, m, α-$CH_2$ Gly), 3.07 (1H, m, β-$CH_{2a}$, His), 2.84 (1H, m, (—$CH_{2b}$, His), 2.07 (2H, t, J=7.8 Hz, $CH_2$ Pal), 1.40 (2H, m, $CH_2$ Pal), 1.23 (24H, brs, $CH_2$ Pal), 0.85 (3H, t, J=6.9 Hz, $CH_3$ Pal).

MS (EI) m/z: 451.4 ($M^+$+1, bp).

Example 15

Evaluation of Gelation of Lipid Peptides with Pure Water

Each of the lipid peptides synthesized in Examples 1, 6, 7, 8, and 10 was placed in a sample tube. Pure water (without metals and ions) was added so that a solution would have a lipid peptide concentration of 0.25 or 0.5% (w/v) (w means mass (g), and v means volume (mL)). The mixture was heated at 90° C. or more to dissolve the lipid peptide, and then allowed to cool.

After allowing to cool, a state where the solution had no flowability and did not run off even when the sample tube was placed in reverse was determined as "gelation (O)". The results are shown in Table 1.

TABLE 1

Evaluation of Gelation of Lipid Peptide with Pure Water

| | | 0.50% (w/v) Gelation | 0.25% (w/v) Gelation |
|---|---|---|---|
| Example 1 | N-palmitoyl-Gly-His•TFA salt | O | O |
| Example 6 | N-lauroyl-Gly-His•TFA salt | O | O |
| Example 7 | N-behenoyl-Gly-His•TFA salt | O | O |
| Example 8 | N-myristoyl-Gly-His•TFA salt | O | O |
| Example 10 | N-palmitoyl-Ala-His•TFA salt | O | O |

Example 16

Evaluation of Gelation of Lipid Peptides with Buffer

Each of the lipid peptides synthesized in Examples 3 to 10 and Example 14 was placed in a sample tube. Each of three phosphate buffers (PBS) (pH=2.6, 7.4, or 10) was added so that a solution would have a lipid peptide concentration of 0.25 or 0.5% (w/v) (conditions A to F). Then, the mixture was heated at 90° C. or more to dissolve the lipid peptide, and then allowed to cool.

After allowing to cool, a state where the solution had no flowability and did not run off even when the sample tube was placed in reverse was determined as "gelation". The results are shown in Table 2. In Table, a sample that formed a gel is shown as "O", a sample that did not form a gel is shown as "X", and a sample without evaluation is shown as "-".

TABLE 2

Evaluation of Gelation of Lipid Peptide with Phosphate Buffer

| | | A | B | C | D | E | F |
|---|---|---|---|---|---|---|---|
| | | pH = 2.6 | | pH-7.4 | | pH = 10 | |
| | | 0.5% (w/v) Gelation | 0.25% (w/v) Gelation | 0.5% (w/v) Gelation | 0.25% (w/v) Gelation | 0.5% (w/v) Gelation | 0.25% (w/v) Gelation |
| Example 1 | N-palmitoyl-Gly-His•TFA salt | O | O | O | O | O | — |

TABLE 2-continued

Evaluation of Gelation of Lipid Peptide with Phosphate Buffer

| | | A | B | C | D | E | F |
|---|---|---|---|---|---|---|---|
| | | pH = 2.6 | | pH-7.4 | | pH = 10 | |
| | | 0.5% (w/v) Gelation | 0.25% (w/v) Gelation | 0.5% (w/v) Gelation | 0.25% (w/v) Gelation | 0.5% (w/v) Gelation | 0.25% (w/v) Gelation |
| Example 6 | N-lauroyl-Gly-His•TFA salt | ○ | ○ | ○ | ○ | ○ | ○ |
| Example 7 | N-behenoyl-Gly-His•TFA salt | ○ | — | ○ | ○ | ○ | — |
| Example 8 | N-myristoyl-Gly-His•TFA salt | ○ | ○ | ○ | ○ | ○ | — |
| Example 10 | N-palmitoyl-Ala-His•TFA salt | ○ | ○ | ○ | ○ | ○ | — |
| Example 11 | N-palmitoyl-Val-His•TFA salt | — | — | ○ | ○ | ○ | — |
| Example 14 | N-palmitoyl-His-Gly•TFA salt | — | — | ○ | ○ | ○ | — |

As shown in Table 2, in an acidic region (pH=2.6), at a concentration of 0.5%, N-palmitoyl-Gly-His.TFA salt, N-lauroyl-Gly-His.TFA salt, N-behenoyl-Gly-His.TFA salt, N-myristoyl-Gly-His.TFA salt, and N-palmitoyl-Ala-His.TFA salt formed gels. At a concentration of 0.25%, N-palmitoyl-Gly-His.TFA salt, N-lauroyl-Gly-His.TFA salt, N-myristoyl-Gly-His.TFA salt, and N-palmitoyl-Ala-His.TFA salt formed gels.

In a neutral region (pH=7.4), all of the lipid peptides used in Example 16 formed gels at each of concentrations of 0.25 and 0.5%.

In contrast, in a basic region (pH=10), all of the lipid peptides used in Example 16 formed gels at a concentration of 0.5%, but at a concentration of 0.25%, only N-lauroyl-Gly-His.TFA salt formed a gel.

Example 17

Evaluation of Gelation of N-Palmitoyl-Gly-His.TFA Salt with Various Solutions

Each N-palmitoyl-Gly-His trifluoroacetate synthesized in Examples 1 to 3 was placed in a screw tube (Maruemu No. 1, manufactured by Maruemu Corp.). Each of various solutions shown in Table 3 was added so as to have an N-palmitoyl-Gly-His.TFA salt (also called Pal-GH (TFA)) concentration of 0.5 or 1% (w/v). The mixture was heated at 100° C. with a constant temperature heat block (manufactured by Nippon Genetics Co., Ltd.), and then allowed at room temperature.

A state where the solution had no flowability and did not run off even when the screw tube was placed in reverse was determined as "gelation", and the gel state was observed. The obtained results are shown in Table 3.

Each N-palmitoyl-Gly-His trifluoroacetate synthesized in Examples 1 to 3 is shown without distinction in Table 3 because each showed similar gelation properties.

TABLE 3

Evaluation of Gelation of N-Palmitoyl-Gly-His (TFA) with Various Solutions

| Solvent | Pal-GH (TFA) concentration % (w/v) | Gel state |
|---|---|---|
| 50% liquid paraffin aqueous solution | 0.5 | White gel |
| 50% propylene glycol aqueous solution | 0.5 | White gel |

TABLE 3-continued

Evaluation of Gelation of N-Palmitoyl-Gly-His (TFA) with Various Solutions

| Solvent | Pal-GH (TFA) concentration % (w/v) | Gel state |
|---|---|---|
| 50% 1,3-butanediol aqueous solution | 0.5 | White gel |
| 50% polyethylene glycol 400 aqueous solution | 0.5 | White gel |
| Polyethylene glycol 400 | 1.0 | Transparent gel |
| 50% glycerin aqueous solution | 0.5 | White gel |
| 70% glycerin aqueous solution | 0.5 | Transparent gel |
| Glycerin | 1.0 | Transparent gel |

Example 18

Evaluation of Gelation of Phosphate Buffer Using N-Palmitoyl-Gly-His.TFA Salt and N-Palmitoyl-Gly-Gly-Gly-His.TFA Salt N-palmitoyl-Gly-Gly-Gly-His.TFA salt used in Example 18 and Example 19 described later were synthesized as below.

About 390 mg of histidine Barlos Resin (Watanabe Chemical Industries, Ltd.) was charged into a PD-10 column. The column was washed with 5 ml of dichloromethane (DCM) three times and further washed with 5 ml of dimethylformamide (DMF) three times. Next, about 270 mg of Fmoc-Gly-OH (Watanabe Chemical Industries, Ltd.) and 2.1 ml of a condensing agent solution 1 (dissolving 3.05 g of HBTU and 1.25 g of HOBt in 16 ml of DMF) were charged, and 2.1 ml of a condensing agent solution 2 (dissolving 2.75 ml of DIPEA in 14.25 ml of DMF) was further charged.

The contents were stirred for 30 minutes with a vibrator, and then washed with 5 ml of DMF five times, subsequently with 5 ml of DCM three times, and then with 5 ml of DMF three times.

Next, 5 ml of 20% piperidine/DMF solution was charged, and the whole was stirred for 1 minutes. The solution was removed, and then 5 ml of 20% piperidine/DMF solution was charged again. The whole was stirred for 45 minutes, and washed with 5 ml of DMF five times.

Furthermore, 270 mg of Fmoc-Gly (Watanabe Chemical Industries, Ltd.), 2.1 ml of the condensing agent 1, and 2.1 ml of the condensing agent 2 were charged. The whole was stirred for 20 minutes with a vibrator, and then washed with 5 ml of DMF five times, with 5 ml of DCM three times, and then with 5 ml of DMF three times. Then, 5 ml of 20% piperidine/DMF solution was charged, and the whole was stirred for 1 minutes. Then, the solution was removed, and 5 ml of 20% piperidine/DMF solution was charged again. The whole was stirred for 45 minutes, and washed with 5 ml of DMF five times.

About 230 mg of palmitic acid (Tokyo Chemical Industry Co., Ltd.) was charged into the column, 2.1 ml of the condensing agent 1 and 2.1 ml of the condensing agent 2 were charged, and the whole was stirred for 90 minutes with a vibrator. After the reaction, the mixture was washed with 5 ml of DMF five times, subsequently with 5 ml of DCM five times, and further with 5 ml of methanol five times, and then the resin was dried overnight under vacuum.

After drying, 3.8 ml of trifluoroacetic acid and 0.1 ml of triisopropylsilane were charged into the column and the whole was stirred for 1 hour.

To the recovered mixed solution, water was added to form a precipitate, and the product was filtered by suction under vacuum. After freeze-drying, the product was washed with 4 ml of acetonitrile three times to give a target compound.

FT-MS$^+$ m/z calc. for $C_{26}H_{46}N_5O_5$ [M+H]$^+$ 507.34207. found 507.92.

N-palmitoyl-Gly-His.TFA salt (10.4 mg) containing 5% by mass of N-palmitoyl-Gly-Gly-His.TFA salt was placed into a screw tube (Maruemu Corp., No. 3), and a phosphate buffer (phosphate buffer powder manufactured by Wako Pure Chemical Industries, Ltd., 1/15 mol/L, pH=7.4, composition: $Na_2HPO_4$ 7.6 g, $KH_2PO_4$ 1.8 g/L) was added so as to have a concentration of 0.5% (w/v). The whole was heated with a dry bath incubator (manufactured by First Gene) (105° C., for 10 minutes). After allowing to cool, a state where the solution had no flowability and did not run off even when the sample tube was placed in reverse was ascertained and determined as gelation.

N-palmitoyl-Gly-His.TFA salt containing 5% N-palmitoyl-Gly-Gly-His.TFA salt was determined to form a gel by heat at a concentration of 0.5% (w/v) in a phosphate buffer medium.

Example 19

Evaluation of Gelation of Ultrapure Water Using N-Palmitoyl-Gly-His.TFA Salt and N-Palmitoyl-Gly-Gly-Gly-His.TFA Salt N-palmitoyl-Gly-His.TFA salt (10.4 mg) containing 5% N-palmitoyl-Gly-Gly-His.TFA salt was placed into a screw tube (Maruemu Corp., No. 3), and ultrapure water (manufactured by Kurita Water Industries Ltd.) was added so as to have a concentration of 1% (w/v). The whole was heated with a dry bath incubator (manufactured by First Gene) (105° C., for 10 minutes). After allowing to cool, a state where the solution had no flowability and did not run off even when the sample tube was placed in reverse was ascertained and determined as gelation.

N-palmitoyl-Gly-His.TFA salt containing 5% N-palmitoyl-Gly-Gly-His.TFA salt was determined to form a gel by heat at a concentration of 1% (w/v) in ultrapure water as a medium.

Example 20

Preparation of Gel and Gel Sheet Using N-Palmitoyl-Gly-His Trifluoroacetate in Water as Medium Into a screw tube (Maruemu No. 3, manufactured by Maruemu Corp.), 3 mg of N-palmitoyl-Gly-His (TFA) prepared in Example 1 was placed, and 0.6 ml of Japanese Pharmacopoeia purified water (Kyoei Pharmaceutical Industries, Ltd.) was added into the screw tube so as to have a concentration of 0.5% (w/v). The whole was heated at 105° C. for 5 minutes, and then allowed to stand at room temperature to prepare a gel of 0.5% N-palmitoyl-Gly-His (TFA).

To the gel, 2 ml of Japanese Pharmacopoeia purified water (Kyoei Pharmaceutical Industries, Ltd.) was further added and sheet formation was observed from a wide view for 72 hours. The N-palmitoyl-Gly-His (TFA) gel prepared in a water medium was not dissolved during water immersion and the formation of a sheet-shaped gel was observed.

Example 21

Preparation of Gel and Gel Sheet Using N-Palmitoyl-Gly-His Trifluoroacetate in Glycerin Solution as Medium Into a screw tube (Maruemu No. 3, manufactured by Maruemu Corp.), 9.1 mg of N-palmitoyl-Gly-His.TFA salt prepared in Example 1 was placed, and 0.91 ml of Japanese Pharmacopoeia purified water (Kyoei Pharmaceutical Industries, Ltd.) and 0.91 ml of glycerin (Junsei Chemical Co., Ltd.) were added into the screw tube so as to have a concentration of 0.5% (w/v). The whole was heated at 105° C. for 5 minutes, and then allowed to stand at room temperature to prepare a gel of 0.5% N-palmitoyl-Gly-His.TFA salt in a glycerin solution.

Into the gel, 2 ml of Japanese Pharmacopoeia purified water (Kyoei Pharmaceutical Industries, Ltd.) was further added and sheet formation was observed from a wide view for 72 hours. The gel of N-palmitoyl-Gly-His.TFA salt prepared in the glycerin solution as a medium was not dissolved during water immersion and the formation of a sheet-shaped gel was observed.

Example 22

Preparation of Gel and Gel Sheet Using N-Palmitoyl-Gly-His Trifluoroacetate in Glycerin as Medium Into a screw tube (Maruemu No. 3, manufactured by Maruemu Corp.), 4.6 mg of N-palmitoyl-Gly-His.TFA salt prepared in Example 1 was placed, and 0.46 ml of glycerin was added into the screw tube so as to have a concentration of 1% (w/v). The whole was heated at 105° C. for 5 minutes, and then allowed to stand at room temperature to prepare a gel of 1% N-palmitoyl-Gly-His.TFA salt in glycerin.

Into the gel, 2 ml of Japanese Pharmacopoeia purified water (Kyoei Pharmaceutical Industries, Ltd.) was further added and sheet formation was observed from a wide view for 72 hours. The gel of N-palmitoyl-Gly-His.TFA salt prepared in glycerin as a medium was not dissolved during water immersion and the formation of a sheet-shaped gel was observed.

Example 23

Evaluation of Gelation of Free N-Palmitoyl-Gly-His in Water and at Various pHs

Free N-palmitoyl-Gly-His prepared in Example 4 was placed into a screw tube (Maruemu No. 1, manufactured by Maruemu Corp.). Each of the various solutions shown in Table 4 was added into the screw tube so as to have a free N-palmitoyl-Gly-His (also called Pal-GH (free)) concentration of 0.1%, 0.2%, 0.5%, 1%, or 2% (w/v). The mixture was heated at 100° C. with a constant temperature heat block (manufactured by Nippon Genetics Co., Ltd.), and then allowed to stand at room temperature.

After allowing to cool, a state where the solution had no flowability and did not run off even when the screw tube was placed in reverse was determined as "gelation". The results are shown in Table 4. In Table, a sample that formed a gel is shown as "O", a sample that formed a sol is shown as "X", and a sample without evaluation is shown as "-".

TABLE 4

Evaluation of Gelation of Free N-Palmitoyl-Gly-His in Various pH Solutions

| Pal-GH (free) concentration % (w/v) | Water | Phosphoric acid aqueous solution pH 2 | pH 3 | Phosphate buffer solution pH 5 | pH 6 | pH 7.5 | pH 9 | pH 10 |
|---|---|---|---|---|---|---|---|---|
| 0.1 | X | O | O | — | — | — | — | — |
| 0.2 | X | O | O | O | O | — | — | — |
| 0.5 | X | O | O | O | O | O | X | X |
| 1.0 | O | — | — | O | O | O | O | O |
| 2.0 | O | — | — | — | — | — | O | O |

Example 24

Evaluation of Gelation of Free N-Palmitoyl-Gly-His in Glycerin Solution

Free N-palmitoyl-Gly-His prepared in Example 4 was placed into a screw tube (Maruemu No. 1, manufactured by Maruemu Corp.). Each of the glycerin solutions having various concentrations shown in Table 5 was added into the screw tube so as to have a free N-palmitoyl-Gly-His concentration of 0.2%, 0.25%, 0.5%, or 1% (w/v). The mixture was heated at 100° C. with a constant temperature heat block (manufactured by Nippon Genetics Co., Ltd.), and then allowed to stand at room temperature.

A state where the solution had no flowability and did not run off even when the screw tube was placed in reverse was determined as "gelation". The obtained results are shown in Table 5. In Table, a sample that formed a gel is shown as "O", a sample that partially formed a gel is shown as "A", and a sample without evaluation is shown as "-".

TABLE 5

Evaluation of Gelation of Free N-Palmitoyl-Gly-His in Glycerin Solution

| Pal-GH (free) concentration % (w/v) | Mass fraction (glycerin/water + glycerin) | | | | | |
|---|---|---|---|---|---|---|
| | 0.1 | 0.3 | 0.4 | 0.5 | 0.6 | 0.7 |
| 1.0 | O | O | O | O | O | O |
| 0.5 | O | O | O | O | O | O |
| 0.25 | O | O | O | O | O | O |
| 0.2 | A | A | — | O | O | O |

Example 25

Evaluation of Gelation of Free N-Palmitoyl-Gly-His in Propylene Glycol (PG) Solution Free N-palmitoyl-Gly-His prepared in Example 4 was placed into a screw tube (Maruemu No. 1, manufactured by Maruemu Corp.). Each of the propylene solutions having various concentrations shown in Table 6 was added into the screw tube so as to have a free N-palmitoyl-Gly-His concentration of 0.25%, 0.5%, or 1% (w/v). The mixture was heated at 100° C. with a constant temperature heat block (manufactured by Nippon Genetics Co., Ltd.), and then allowed to stand at room temperature.

A state where the solution had no flowability and did not run off even when the screw tube was placed in reverse was determined as "gelation". The obtained results are shown in Table 6. In Table, a sample that formed a gel is shown as "O", a sample that partially formed a gel is shown as "A", and a sample that formed no gel is shown as "X".

TABLE 6

Evaluation of gelation of free N-palmitoyl-Gly-His in PG solution

| Pal-GH (free) concentration % (w/v) | Mass fraction (PG/water + PG) | | | | | |
|---|---|---|---|---|---|---|
| | 0.1 | 0.2 | 0.3 | 0.5 | 0.7 | 1.0 |
| 1.0 | O | O | O | O | O | X |
| 0.5 | A | A | O | O | O | X |
| 0.25 | A | A | A | O | O | X |

Example 26

Evaluation of Gelation of Free N-Palmitoyl-Gly-His in Solution Containing Inorganic Salt, Amino Acid, or Organic Substance Free N-palmitoyl-Gly-His prepared in Example 4 was placed into a screw tube (Maruemu No. 1, manufactured by Maruemu Corp.). An aqueous solution dissolving each additive described in Table 7 was added into the screw tube so as to have a free N-palmitoyl-Gly-His concentration of 0.5% or 1% (w/v). The mixture was heated at 100° C. with a constant temperature heat block (manufactured by Nippon Genetics Co., Ltd.), and then allowed to stand at room temperature.

A state where the solution had no flowability and did not run off even when the screw tube was placed in reverse was determined as "gelation". The obtained results are shown in Table 7. In Table, a sample that formed a gel is shown as "O", a sample that partially formed a gel is shown as "A", and a sample without evaluation is shown as "-".

TABLE 7

Evaluation of Gelation of Free N-Palmitoyl-Gly-His in Solution Containing Inorganic Salt, Amino Acid, or Organic Substance

| Additive | Additive concentration | Pal-GH (free) concentration % (w/v) | |
|---|---|---|---|
| | | 0.5 | 1.0 |
| Phenoxyethanol | 0.25 wt % | O | O |
| Glycine | 0.1 wt % | O | — |
| Alanine | 0.1 wt % | O | — |
| Lysine hydrochloride | 0.1 wt % | A | — |
| Aspartic acid | 0.27 wt % | O | — |
| NaCl | 0.1 wt % | A | O |
| | 0.5 wt % | O | O |
| KCl | 0.1 wt % | A | O |
| | 0.5 wt % | A | O |

Example 27

Evaluation of Gelation of 0.25% (w/v) Free N-Palmitoyl-Gly-His in Propylene Glycol Aqueous Solution (65% (w/w)) (Containing Lactic Acid and Potassium Lactate)

Free N-palmitoyl-Gly-His (25 mg) obtained in Example 4 was placed in a screw tube (Maruemu Corp., No. 7). Sixty-five percent (w/w) propylene glycol aqueous solution was added so as to have a concentration of 0.25% (w/v), and a mixture of potassium lactate:lactic acid (95:5) was further added so as to have a concentration of 5% (w/w) with respect to the whole solution. The mixture was heated with a dry bath incubator (manufactured by First Gene) at 75° C. for 10 minutes. The obtained solution was transferred into a spray vial (Maruemu Corp., No. 3L), and allowed to cool to room temperature.

After allowing to cool, a state where the solution had no flowability and did not run off even when the sample tube was placed in reverse was ascertained and determined as gelation.

Example 28

Evaluation of Gelation of 0.2% (w/v) Free N-Palmitoyl-Gly-His in Propylene Glycol Aqueous Solution (65% (w/w)) (Containing Lactic Acid and Potassium Lactate)

Free N-palmitoyl-Gly-His (80 mg) obtained in Example 4 was placed into a screw tube (Maruemu Corp., No. 7). Sixty-five percent (w/w) propylene glycol aqueous solution was added so as to have a concentration of 0.2% (w/v), and a mixture of potassium lactate:lactic acid (95:5) was further added so as to have a concentration of 5% (w/w) with respect to the whole solution. The mixture was heated with a dry bath incubator (manufactured by First Gene) at 93° C. for 5 minutes. The obtained solution was transferred into a spray vial (Maruemu Corp., No. 3L), and allowed to cool to room temperature.

After allowing to cool, a state where the solution had no flowability and did not run off even when the sample tube was placed in reverse was ascertained and determined as gelation.

Example 29

Preparation of Gel and Gel Sheet Using N-Palmitoyl-Gly-His'TFA Salt in Glycerin and Polyethylene Glycol 400 as Medium (1)

Each of the 50.4 mg of N-palmitoyl-Gly-His.TFA salt prepared in Examples 1 to 3 was placed into a screw tube (Maruemu No. 7, manufactured by Maruemu Corp.). Into the screw tube, 1 ml of polyethylene glycol 400 (Wako Pure Chemical Industries, Ltd.), 1.5 ml of ethanol, and 8 ml of 70% glycerin (Junsei Chemical Co.) in water were added so as to have an N-palmitoyl-Gly-His TFA salt concentration of 0.5% (w/v). The mixture was heated with a dry bath incubator (manufactured by First Gene) (105° C., for 8 minutes), and then allowed to stand at room temperature to form a gel.

Into the gel, 20 ml of Japanese Pharmacopoeia purified water (Kyoei Pharmaceutical Industries, Ltd.) was further added and whether sheet formation occurred or not was observed from a wide view for 72 hours. The gels of N-palmitoyl-Gly-His.TFA salt prepared in glycerin and polyethylene glycol 400 as a medium were not dissolved during water immersion and the formation of a sheet-shaped gel was observed.

Example 30

Preparation of Gel and Gel Sheet Using N-Palmitoyl-Gly-His.TFA Salt in Glycerin and Polyethylene Glycol 400 as Medium (2)

Each of the 52.5 mg of N-palmitoyl-Gly-His.TFA salt prepared in Examples 1 to 3 was added into a screw tube (Maruemu No. 7, manufactured by Maruemu Corp.). Into the screw tube, 0.5 ml of polyethylene glycol 400 (Wako Pure Chemical Industries, Ltd.), 1 ml of ethanol, and 8 ml of 70% glycerin (Junsei Chemical Co.) in water were added so as to have an N-palmitoyl-Gly-His.TFA salt concentration of 0.5% (w/v). The mixture was heated with a dry bath incubator (manufactured by First Gene) (105° C., for 8 minutes), and then allowed to stand at room temperature to form a gel.

Into the gel, 20 ml of Japanese Pharmacopoeia purified water (Kyoei Pharmaceutical Industries, Ltd.) was further added and whether sheet formation occurred or not was observed from a wide view for 72 hours. The gels of N-palmitoyl-Gly-His.TFA salt prepared in glycerin and polyethylene glycol 400 as a medium were not dissolved during water immersion and the formation of a sheet-shaped gel was observed.

Example 31

N-Palmitoyl-Gly-His (TFA) Gel Sheet Including Indomethacin and I-Menthol

Each of the 50.2 mg of palmitoyl-Gly-His.TFA salt prepared in Examples 1 to 3 was placed into a screw tube (Maruemu No. 7, manufactured by Maruemu Corp.) together with 104.7 mg of indomethacin and 220 mg of I-menthol. Into the screw tube, 0.5 ml of polyethylene glycol 400 (Wako Pure Chemical Industries, Ltd.), 1.5 ml of ethanol, 8 ml of 70% glycerin (Junsei Chemical Co., Ltd.) in water were added so as to have an N-palmitoyl-Gly-His.TFA salt concentration of 0.5% (w/v). The mixture was heated with a dry bath incubator (manufactured by First Gene) (105° C., for 8 minutes), and then allowed to stand at room temperature to form a pale yellow gel. The texture of the gel was smooth and cool.

After ascertainment of the gel formation, the gel was allowed to stand at room temperature for 45 days. Then, 20 ml of Japanese Pharmacopoeia purified water (Kyoei Pharmaceutical Industries, Ltd.) was added and sheet formation was observed from a wide view for 72 hours. The gel was not dissolved during water immersion and the formation of a sheet-shaped gel was observed.

Example 32

Incorporation Test of 6-Anilino-1-Naphthalenesulfonic Acid (ANS) into Fiber Formed by Self-Organization of N-Palmitoyl-Gly-His Trifluoroacetate In pH 7.5 phosphate buffer, 8-anilino-1-naphthalenesulfonic acid (ANS) as a hydrophobic environment responsive probe was dissolved so as to have a final concentration of 5 µM. Into the solution, N-palmitoyl-Gly-His.TFA salt prepared in Example 1 was added so as to have a concentration of 0.5 wt % to prepare a gel.

Separately, as controls, only N-palmitoyl-Gly-His.TFA salt was added at a concentration of 0.5 wt % into pH 7.5 phosphate buffer to prepare a gel, and pH 7.5 phosphoric acid aqueous solution dissolving 5 µM ANS (without N-palmitoyl-Gly-His.TFA salt) was prepared.

On each of the gels and the solution, the fluorescence intensity was measured (excitation wavelength (ex) at 350 nm, fluorescence wavelength (em) at 480 nm). The obtained results are shown in FIG. 2.

Figure 2:
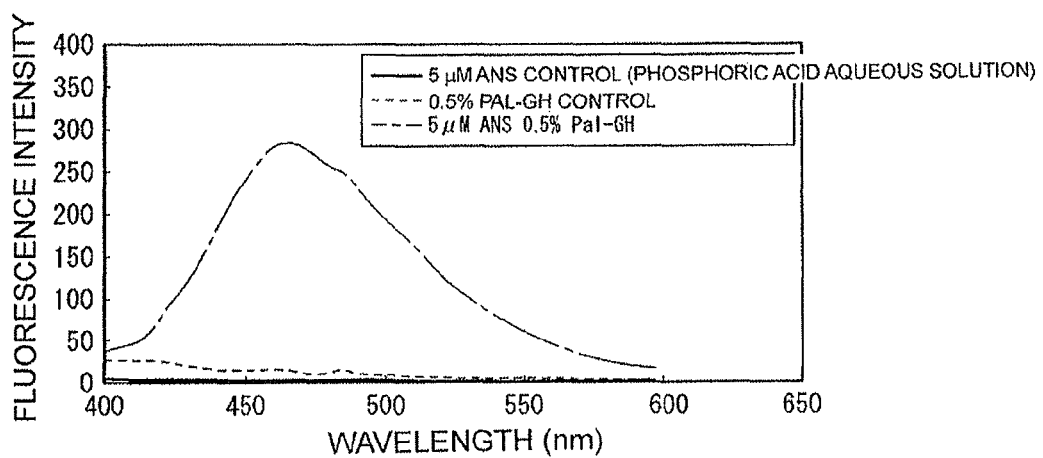
FIG. 2 is a figure showing fluorescence intensities measured on two gels and a solution prepared in Example 32.

As shown in FIG. 2, 5 µM ANS in pH 7.5 phosphoric acid aqueous solution and the gel of 0.5 wt % N-palmitoyl-Gly-His (TFA) in pH 7.5 phosphoric acid aqueous solution showed little fluorescence intensity, but the gel of 0.5 wt % N-palmitoyl-Gly-His (TFA) in pH 7.5 phosphoric acid aqueous solution including ANS showed strong fluorescence intensity at around 460 nm. The results revealed that ANS was incorporated into the fiber formed by self-organization of N-palmitoyl-Gly-His (TFA) (inclusion compound was formed).

In a similar manner to the above case, each of 0.5 wt % agarose gel, 3 wt % sodium alginate gel, and 5 wt % polyacrylamide gel was prepared using ANS that was dissolved in pH 7.5 phosphate buffer so as to have a final concentration of 5 µM. However, ANS in each gel showed little fluorescence intensity as with ANS in the phosphoric acid aqueous solution.

Example 33

Solubilization Test of Hydrophobic Substance by N-Palmitoyl-Gly-His Trifluoroacetate DL-α-tocopherol (vitamin E) as a hydrophobic substance was dissolved in ethanol to prepare a stock solution. The stock solution was diluted with a phosphate buffer (pH 7.5) to prepare each sample solution having a final vitamin E concentration of 100 µM to 500 µM (containing 5% ethanol).

To each sample solution, N-palmitoyl-Gly-His.TFA salt prepared in Example 1 was added (a final concentration: 0.2 wt %). The whole was heated and dissolved, and then allowed to cool to make a gel.

When N-palmitoyl-Gly-His.TFA salt was added, the mixture became transparent immediately after heating, and formed no precipitate even after allowing to cool. That is, the obtained result revealed that vitamin E could be solubilized in the gel. In contrast, when N-palmitoyl-Gly-His.TFA salt was not added, vitamin E could not be solubilized and precipitates were observed.

The results show that a gel including vitamin E can be prepared by using N-palmitoyl-Gly-His.TFA salt.

Example 34

Figure 3:
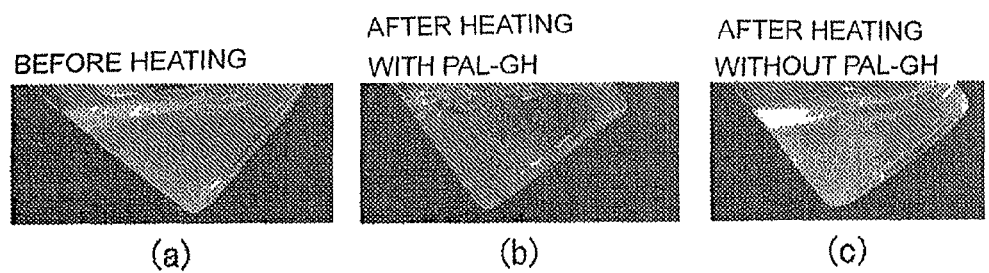
FIG. 3 is views showing solubilization of a milky solution containing vitamin E and a vitamin C derivative prepared in Example 34.

Simultaneous Solubilization Test of Vitamin C Derivative and Vitamin E by Free N-Palmitoyl-Gly-His An ethanol solution of 1 wt % DL-α-tocopherol (vitamin E) was prepared. Separately, L(+)-ascorbic acid diphosphate trisodium (vitamin C derivative) was dissolved in a phosphate buffer (pH 7.4) so as to have a concentration of 0.1 wt % to prepare a stock solution. When the ethanol solution of vitamin E and the stock solution of the vitamin C derivative were mixed at 1:99, the mixture became milky (FIG. 3(a)).

Next, free N-palmitoyl-Gly-His prepared in Example 4 was added to the milky solution so as to have a final concentration of 1 wt %, the whole was heated with a dry bath incubator for 10 minutes so as to become a temperature of 80° C. The mixture without free N-palmitoyl-Gly-His remained milky (FIG. 3(c)). In contrast, the mixture with free N-palmitoyl-Gly-His became clear and colorless (FIG. 3(c)). The result revealed that vitamin E and the vitamin C derivative could be completely and simultaneously solubilized in the gel. The gel formed no precipitate of vitamin E and the vitamin C derivative even when the gel was allowed to cool to room temperature.

The results reveal that a gel simultaneously including vitamin E and the vitamin C derivative, which have different solubilities from each other, can be prepared by using free N-palmitoyl-Gly-His.

Example 35

Gelation Test of Free N-Palmitoyl-Gly-His when Adding Methylparaben

An aqueous solution of 0.2 wt % methylparaben was prepared, and into the solution, free N-palmitoyl-Gly-His prepared in Example 4 was added so as to have a concentration of 0.25, 0.5, or 1.0 wt % to prepare a suspended mixture solution. Each mixture solution was heated at 95 to 99° C. until dissolved (for 6 to 25 minutes), and then allowed to cool to room temperature. As a result, a transparent gel was obtained at a concentration of 0.5 wt % or more.

When comparing with the condition of water alone shown in Example 23, the obtained results reveal that free N-palmitoyl-Gly-His accelerates the dissolution of methylparaben with poor solubility as well as improves the own gelation properties by adding methylparaben.

Detailed mechanisms of the improvement of gelation properties by addition of methylparaben were unknown. One of the probable reasons is that the distance between the amide group of the peptide bond part and the terminal carboxy group in N-palmitoyl-Gly-His matches the distance between the hydroxy group and the carboxy group in methylparaben, and then methylparaben breaks in between N-palmitoyl-Gly-His molecules to form assembly through hydrogen bonds.

Another probable reason is that the imidazole ring of histidine in N-palmitoyl-Gly-His and the aromatic ring of methylparaben are π-stacked, a hydrogen bond is formed between the carboxy group of methylparaben and the carboxy group of histidine, and then the assembly of methylparaben between N-palmitoyl-Gly-His molecules is formed.

Example 36

Preparation of Film Using N-Palmitoyl-Gly-His Trifluoroacetate

Into a screw tube (Maruemu No. 3, manufactured by Maruemu Corp.), 3 mg of N-palmitoyl-Gly-His.TFA salt prepared in Example 1 was placed. Into the screw tube, 0.6 ml of Japanese Pharmacopoeia purified water (Kyoei Pharmaceutical Industries, Ltd.) was added so as to have a concentration of 0.5% (w/v). The whole was heated at 105° C. for 5 minutes, and then allowed to stand at room temperature to prepare a gel of 0.5% N-palmitoyl-Gly-His.TFA salt.

Into the gel, 2 ml of Japanese Pharmacopoeia purified water (Kyoei Pharmaceutical Industries, Ltd.) was further added and sheet formation was observed from a wide view for 72 hours. The N-palmitoyl-Gly-His (TFA) gel prepared in water as a medium did not dissolve during water immersion and the formation of a sheet-shaped gel was observed.

Furthermore, when the obtained gel sheet was transferred onto a glass substrate and left in a desiccator for over ten days, water as the medium evaporated and a film of N-palmitoyl-Gly-His.TFA salt was prepared.

Example 37

Preparation of Glycerin Film by Free N-Palmitoyl-Gly-His

Using 10 mg of free N-palmitoyl-Gly-His, each 2.0 mL of 30%, 20%, and 10% glycerin aqueous solutions was added so as to become a 0.5% (w/v) solution, and the mixture solution was heated and dissolved at 80° C. The solution was placed in a glass petri dish having an inner diameter of 2.2 cm and allowed to cool at room temperature. After allowing to cool, a state where the solution had no flowability and did not run off even when the glass petri dish was placed in reverse was determined as gelation. Then, the obtained gel was transferred onto a glass substrate.

The gelation was observed in each case using glycerin aqueous solutions having the respective concentrations. Furthermore, when the obtained sheet-shaped gel was left in a desiccator for 10 days, a film of free N-palmitoyl-Gly-His containing glycerin was prepared from each gel.

INDUSTRIAL APPLICABILITY

The gelator including the lipid peptide of the present invention and the gel obtained therefrom can stably keep a gel structure in a wide pH range from an acidic region to an alkaline region, especially in a neutral condition, can form a gel not only from water but also from an alcoholic solution, a hydrophilic organic solution, a hydrophobic organic solution, a higher alcohol, and the like and a mixed solution of such solvent and water, and have very high biocompatibility. Thus, they are preferably used for cosmetic base materials, quasi-drug base materials, and medical external preparations as well as various functional materials such as ink and paint.

For example, from the viewpoint of the application in a wide pH range, preferred applications include detergents (for example, for medical use, home use, and industrial use), sol-gelators (for cosmetics and other commodities), gelators for stabilizing pigment, food additives (for example, for acidic foods, alkaline foods, and neutral foods).

Furthermore, in a neutral region, they can be used for biological and biochemical materials, for example, as cell culture carriers and base materials for skin. In an acidic region, they can be used as base materials for pharmaceutical products such as gastric acid-secretion inhibitors, enteric coated preparations, and biodegradable anti-metabolic syndrome preparations for feeling of fullness, as stabilizers and additives when producing acid milk beverages containing pectin and the like, and for improvement of alkali soils.

Furthermore, in an alkaline region, they can be used as stabilizers and additives when producing alkaline beverages and milk beverages, for catalytic reactions using various alkaline enzymes (such as alkaline protease, alkaline cellulase, alkaline amylase, alkaline xylase, and alkaline pectate lyase), for industrial use of alkalophilic bacteria, as gelators used for alkaline batteries, for improvement of acidic soils, and as base materials, reaction additives, and accelerators in various industrial applications such as bioreactors, detergent and soap, cosmetics, drug discovery, and analyses and tests.

What is claimed is:
1. A gel comprising:
a lipid peptide of Formula (1b):

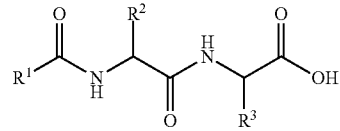

where:
$R^1$ is a $C_{9-23}$ aliphatic group,
$R^2$ is a methyl group, and
$R^3$ is an imidazole methyl group,
or a pharmaceutically usable salt of the lipid peptide; and
a solvent.

2. The gel according to claim 1, wherein the solvent is water, an alcohol, an aqueous solution, an alcoholic solution, a hydrophilic organic solution, a higher alcohol, a fatty acid, higher fatty acid esters, a glyceride, a hydrophobic organic solution, or a miscible mixed solvent thereof.

3. The gel according to claim 2, wherein the solvent is water, an alcohol, an aqueous solution, an alcoholic solution, a hydrophilic organic solution, a higher alcohol, a hydrophobic organic solution, or a miscible mixed solvent thereof.

4. The gel according to claim 2, wherein the alcoholic solution is a mixed solution of at least one alcohol selected from a group consisting of methanol, ethanol, 2-propanol and i-butanol, and water.

5. The gel according to claim 2, wherein the hydrophilic organic solution is a mixed solution of at least one hydrophilic organic solvent selected from a group consisting of acetone, dioxane, glycerin, propylene glycol and polyethylene glycol, and water.

6. The gel according to claim 2, wherein the hydrophobic organic solution is a solution of at least one hydrophobic organic solvent selected from a group consisting of a liquid paraffin, a mineral oil, hydrogenated polyisobutene and olive oil.

7. The gel according to claim 2, wherein the aqueous solution is an aqueous solution dissolving at least one inorganic salt selected from a group consisting of an inorganic carbonate, an inorganic sulfate, an inorganic phosphate, and an inorganic hydrogen phosphate, or at least one organic salt selected from a group consisting of an organic amine hydrochloride and an organic amine acetate.

8. The gel according to claim 7, wherein:
the inorganic salt is at least one inorganic salt selected from a group consisting of calcium carbonate, sodium carbonate, potassium carbonate, sodium sulfate, potassium sulfate, magnesium sulfate, potassium phosphate, sodium phosphate, disodium hydrogen phosphate, and sodium dihydrogen phosphate, and
the organic salt is at least one organic salt selected from a group consisting of ethylenediamine hydrochloride, ethylenediaminetetraacetate, and trishydroxymethylaminomethane hydrochloride.

9. The gel according to claim 1, further comprising an antiseptic.

10. The gel according to claim 1, wherein the gel is a sheet-shaped gel.

11. A film obtained by evaporation of a solvent from the sheet-shaped gel according to claim 10.

12. A method of preparing the gel of claim 1, comprising the steps:
- adding the solvent to the lipid peptide of Formula (1b) or a pharmaceutically usable salt of the lipid peptide,
- heating a resultant mixture at a temperature of 75° C. or more to dissolve the lipid peptide of Formula (1b) or the pharmaceutically usable salt of the lipid peptide; and
- allowing the resulting solution to cool to subject the solution to gelation.

* * * * *